United States Patent
von Olshausen et al.

(10) Patent No.: US 10,421,913 B2
(45) Date of Patent: Sep. 24, 2019

(54) PRODUCTION PROCESS AND PRODUCTION SYSTEM FOR PRODUCING METHANE / GASEOUS AND/OR LIQUID HYDROCARBONS

(71) Applicants: SunFire GmbH, Dresden (DE); Climeworks AG, Zurich (CH)

(72) Inventors: Christian von Olshausen, Dresden (DE); Dietmar Rueger, Bannewitz (DE); Jan Andre Wurzbacher, Zurich (CH); Christoph Gebald, Regensdorf (CH)

(73) Assignees: SunFire GmbH, Dresden (DE); Climeworks AG, Zurich (CH)

( * ) Notice: Subject to any disclaimer, the term of this patent is extended or adjusted under 35 U.S.C. 154(b) by 0 days.

(21) Appl. No.: 15/565,151

(22) PCT Filed: Apr. 7, 2016

(86) PCT No.: PCT/DE2016/100164
§ 371 (c)(1),
(2) Date: Oct. 7, 2017

(87) PCT Pub. No.: WO2016/162022
PCT Pub. Date: Oct. 13, 2016

(65) Prior Publication Data
US 2018/0086985 A1 Mar. 29, 2018

Related U.S. Application Data

(63) Continuation of application No. PCT/DE2015/100148, filed on Apr. 8, 2015.

(30) Foreign Application Priority Data

Apr. 8, 2015 (WO) ................ PCT/DE2015/100148

(51) Int. Cl.
*C10G 2/00* (2006.01)
*B01D 53/04* (2006.01)
(Continued)

(52) U.S. Cl.
CPC ............. *C10G 2/50* (2013.01); *B01D 53/047* (2013.01); *B01D 53/0462* (2013.01); *C07C 1/12* (2013.01);
(Continued)

(58) Field of Classification Search
CPC .. C10G 2400/04; C10G 2400/02; C10G 2/32; C01B 2203/0233; C01B 2203/0238;
(Continued)

(56) References Cited

U.S. PATENT DOCUMENTS

2009/0307975 A1 12/2009 Wolf
2014/0272734 A1 9/2014 Braun et al.

FOREIGN PATENT DOCUMENTS

DE 102007056267 A1 5/2009
EP 1887071 A1 2/2008
(Continued)

OTHER PUBLICATIONS

CN 203648344 (machine translation), Lie et al., carbon dioxide capture experiment evaluation testing device, Jun. 18, 2014.*
(Continued)

*Primary Examiner* — Jafar F Parsa
(74) *Attorney, Agent, or Firm* — Patent Central LLC; Stephan A. Pendorf

(57) ABSTRACT

A process for the production of synthetically produced methane (57)/gaseous and/or liquid hydrocarbons (114, 115, 116, 117). For this purpose, hydrogen (44, 84, 150) from an electrolytic arrangement (41, 81, 151, 159) which is operated by means of regeneratively generated electric energy and carbon dioxide (19, 46, 86) are synthesized in a methane
(Continued)

Figure 1:
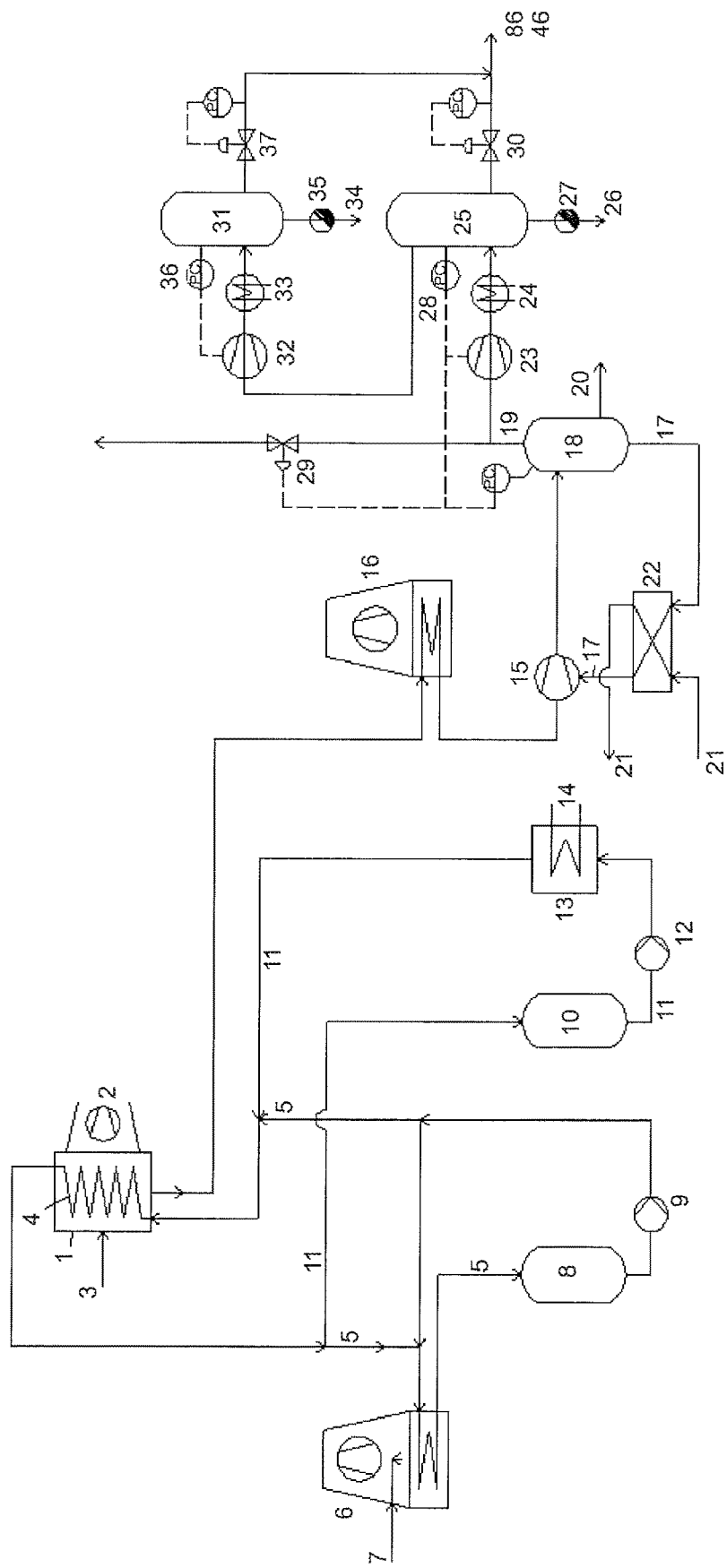

synthesis (FIGS. 2-48) or Fischer-Tropsch synthesis (FIGS. 3-96) or other suitable hydrocarbon synthesis, the carbon dioxide (19, 46, 86) being produced from an air/gas flow (3, 134) by means of a carbon dioxide recovery system (FIG. 1). The carbon dioxide (19, 46, 86) is obtained from the air/gas flow (3, 134) in the carbon dioxide recovery system (FIG. 1) by way of a reversible adsorption process. Also a production system (57) for the production of synthetically produced methane/gaseous and/or liquid hydrocarbons (114, 115, 116, 117), in particular for carrying out the production process according to the invention, comprising an electrolytic arrangement (41, 81, 151, 159) which is operated by means of regeneratively generated electric energy (42, 82, 153) for producing hydrogen (44, 84, 150), a carbon dioxide recovery system (FIG. 1) for producing carbon dioxide (19, 46, 86) from an air/gas flow (3, 134) and a methane (FIG. 2) or Fischer-Tropsch synthesis (FIG. 3) or any other suitable hydrocarbon synthesis for synthesizing hydrogen (44, 84, 150) and carbon dioxide (19, 45, 86) to methane (57)/gaseous and/or liquid hydrocarbons (114, 115, 116, 117).

15 Claims, 12 Drawing Sheets

(51) Int. Cl.
| | | |
|---|---|---|
| B01D 53/047 | (2006.01) | |
| C25B 1/04 | (2006.01) | |
| C25B 15/02 | (2006.01) | |
| C25B 15/08 | (2006.01) | |
| C07C 1/12 | (2006.01) | |
| C07C 9/04 | (2006.01) | |

(52) U.S. Cl.
CPC .............. *C07C 9/04* (2013.01); *C25B 1/04* (2013.01); *C25B 15/02* (2013.01); *C25B 15/08* (2013.01); *B01D 2257/504* (2013.01); *B01D 2259/65* (2013.01); *Y02C 10/08* (2013.01); *Y02C 20/20* (2013.01); *Y02E 60/366* (2013.01); *Y02P 20/129* (2015.11); *Y02P 20/152* (2015.11)

(58) Field of Classification Search
CPC ...... C01B 2203/0283; C01B 2203/043; C01B 2203/0495; C01B 2203/062; C01B 2203/067; C01B 203/0833; C01B 2203/0872; C01B 2203/0148; B01D 2251/602; B01D 2258/0283; B01D 3/384; C25B 1/00
See application file for complete search history.

(56) References Cited

FOREIGN PATENT DOCUMENTS

| EP | 2049232 A1 | 4/2009 |
|---|---|---|
| EP | 2491998 A1 | 8/2012 |
| EP | 2638949 A1 | 9/2013 |
| GB | 2448685 A | 10/2008 |
| WO | 2006004583 A2 | 1/2006 |
| WO | 2008021698 A2 | 2/2008 |
| WO | 2014170184 A1 | 10/2014 |

OTHER PUBLICATIONS

International Search Report dated Jul. 25, 2016, in International Application No. PCT/DE2016/100164.
International Search Report and Written Opinion dated Jan. 8, 2016, in International Application No. PCT/DE2015/100148.

* cited by examiner

PRODUCTION PROCESS AND PRODUCTION SYSTEM FOR PRODUCING METHANE / GASEOUS AND/OR LIQUID HYDROCARBONS

The invention relates to a process for the production of synthetically produced methane/gaseous and/or liquid hydrocarbons, wherein for this purpose hydrogen from an electrolytic arrangement which is operated by means of regeneratively generated electric energy and carbon dioxide are combined in a methane synthesis or Fischer-Tropsch synthesis or other suitable hydrocarbon synthesis as well as a production system for the production of synthetically produced methane/gaseous and/or liquid hydrocarbons.

From the prior art, different systems are known for producing methane or gaseous or liquid hydrocarbons synthetically using electrical energy. Here, such synthesis systems are mainly used for storage of electrical energy that has been produced in regenerative manner, for example by wind or solar power, and constitutes storage of electricity. Further, such synthesis plants are used in general for the production of synthetically produced and $CO_2$-neutral fuels. By way of example, reference may be made to the applicant's publication EP 2 049 232 B which discloses a process for the reprocessing of the combustion products carbon dioxide and water into renewable energy fuels by means of electrical energy from renewable energy sources.

Further, an overall synthesis process is known from EP 1887071 A1, wherein for the production of synthesis gas carbon dioxide can be extracted from process exhaust gases or the normal atmosphere, wherein for extraction the so-called oxyfuel process or, in the case of a power plant, downstream exhaust gas $CO_2$ separation devices are proposed. Particularly preferred for $CO_2$ recovery are however air decomposition devices, which are in use for the generation of nitrogen and/or oxygen. Further, mention can be made of $CO_2$ separation processes using graded membranes.

WO 2008/021698 A2 discloses a process for the production of methane and other products, in which case the necessary carbon dioxide is obtained by absorption or adsorption from dried atmospheric air.

It is also known from WO 2006/004583 A2 that the carbon dioxide required for the production of synthetic liquid hydrocarbons can be taken from seawater or from the ambient air.

From the document GB 2,448,685 a method or an arrangement is known in which carbon dioxide, obtained from the air by absorption or adsorption, is used for the synthesis of liquid hydrocarbons or fuels.

US 2014/0272734 A1 describes processes for producing liquid fuel from the starting materials $CO_2$ and $H_2O$. With respect to $CO_2$ sources, this document only describes combustion gases ("flue gas") [0014, 0027], and wherein there is no mention of atmospheric air as $CO_2$ source. In contrast to this publication, atmospheric air is used as the $CO_2$ source in the present application. Due to the high dilution of $CO_2$ in atmospheric air, there are fundamental differences in the apparatus and associated processes for $CO_2$ capture from air versus flue gases. It should be noted at this point that a flue gas comprises about 300 times more $CO_2$, than is contained in the atmospheric air. The process described in the present disclosure for $CO_2$ separation from air is based on a temperature-vacuum-exchange process for amine-functionalized adsorbents. Due to the low $CO_2$ concentration of $CO_2$ in the air there is a necessity in particular for a pressure reduction and temperature increase for an efficient and gentle regeneration of the adsorbent. The publication US 2014/0272734 A1 describes exclusively pressure swing and thermal shock method (temperature-variation adsorption) [0027] as a possible method for adsorbing. However, a pressure change is not sufficient alone for a deliberate $CO_2$ separation from the air. For regeneration, a temperature change alone would lead to damage to the adsorbent. A main difference in the process management between US 2014/0272734 A1 and the present disclosure is the co-adsorption and co-desorption of $H_2O$. The concentration of $H_2O$ in the atmospheric air is usually an order of magnitude greater than the concentration of $CO_2$, whereas in flue gases the concentration of $H_2O$ is at most comparable to the concentration of $CO_2$, but in most cases is much lower. For this reason, during $CO_2$ extraction from air a significant portion of $H_2O$ is co-adsorbed, which is co-desorbed during the $CO_2$ desorption. The desorption of $H_2O$ has a fundamentally different characteristic than the desorption of $CO_2$, which is why the methods known from the publication US 2014/0272734 A1 can provide no indication of a functioning process for $CO_2$ extraction from air, in particular with respect to a thermal integration. Finally, document US 2014/0272734 A1 mentions that is that the input stream $CO_2$ and $H_2O$ can be mixed with compressed air in the SOEC, however the compressed air is in this case not a $CO_2$ source but rather serves or is obligated to the reduction reaction in the SOEC. Further, in US Patent 2014/0272734 A1 it is mentioned that preheated air is supplied to the electrolysis and reacts with the preheated feed stream to produce a syngas, whereon this idea presumably originates from the operation of the SOFC, where the air takes part in the reaction. In the operation of a SOEC, or co-electrolysis, this type of process is irrelevant. The air only serves to flush away the oxygen cleaved in the electrolysis by electric energy from $H_2O$ and $CO_2$, which accumulates on the anode side. Mainly the $N_2$ content in the air reduces the partial pressure of oxygen on the anode side, which increases the driving force for oxygen transport through the electrolyte. The $CO_2$ contained in the air remains unaffected, since it is located on the anode side and not, like the feed stream, on the cathode side.

The document EP 2 638 949 A1 describes an apparatus and process for $CO_2$ separation from process gas streams, in particular during the production of methanol or ammonia. The process is based on pressure and temperature variation processes for an adsorbent without chemical amine modification. Adsorbents without chemical modification amine, for example zeolites, are not suitable for $CO_2$ capture from the air, as they competitively adsorb $CO_2$ and $H_2O$. Due to the comparatively large $H_2O$ concentration in air, adsorbents adsorb without chemical amine modification when used in atmospheric air mainly $H_2O$ (>10 mmol $H_2O$/g) and little $CO_2$ (<0.1 mmol $CO_2$/g). Adsorbents without chemical modification of amine are then regenerated at comparatively high temperatures of 200° C., as described in the publication EP 2 638 949 A1 [0014]. Amine-functionalized adsorbents, as described in the present disclosure for $CO_2$ extraction from air, function fundamentally different than those described in the EP 2638949 A1: first, this class adsorbents adsorb $CO_2$ in the presence of water (no competitive effect) and, second, these are regenerated at significantly lower temperatures of about 60-100° C. The methods of EP 2 638 949 A1 cannot lead to conclusions as to a functioning process for $CO_2$ extraction from air, especially not with respect to heat integration.

In the prior art document EP 2491998 A1 it is mentioned that $CO_2$ can be derived from exhaust gases of combustion processes or from the environment. A primarily $CO_2$ recovery unit is not disclosed in EP 2491998 A1, whereby an essential feature is missing. In the document EP 2491998 A1 it is proposed to use the water resulting in the process together with additional water for process cooling in the scope of synthesis, and splitting the water vapor thus formed in electrolysis with electric energy into hydrogen and oxygen. The hydrogen is then also inserted with the aid of electric energy for the reduction of $CO_2$ to CO. The synthesis gas produced is used in a synthesis for the production of hydrocarbons. Thus, the main difference between the present disclosure and EP 2491998 A1 is that in the document EP 2491998 A1 water vapor generated from the waste heat of the synthesis process is used in an electrolysis to generate hydrogen and not to provide heat for a $CO_2$ generation process.

The problems in the prior art are essentially the inefficiency of coupled synthesis systems in combination with carbon dioxide recovery systems according to the invention, so that here, in addition to the general desire for improvements, especially in energy efficiency, is of great importance, in which resources should be conserved and the aspect of neutrality in terms of energy use are of prime importance.

In particular, it has been recognized that, in the case of synthesis plants in the prior art, a large portion of unused waste heat is present, whose energy should be made useable.

Further, it has been found that the prior art does not solve the problem of fluctuating availability of regenerative energy.

The object of the present invention is concerned with the task of providing a production process and a production system which is a resource-saving and enables efficient production of synthetically produced methane or gaseous and/or liquid hydrocarbons, preferably from fluctuating available energy, wherein individual plant parts with inherent disadvantages are synergistically connected together into an overall system and, in particular make use of usable waste heat of the synthesis plant.

This object is achieved with a production process according to the main claim and of a production system according to an alternative claim.

The carbon dioxide is produced from an air/gas stream by means of a carbon dioxide separator unit or generator, such as described, for example, in WO 2014/170184 A1, wherein the carbon dioxide from the air/gas stream is firstly adsorbed in the carbon dioxide separator unit by means of an adsorption material, which is preferably functionalized with amine groups (primary, secondary, tertiary amines) (covalent or physical bonding of the amines), at ambient temperature and pressure, wherein for reversing the adsorption process and thus to release the adsorbed carbon dioxide a temperature-vacuum-variation process is conducted, wherein for this heat is introduced into the adsorber and the pressure around the adsorbent material is lowered and the heat at least partly derived from the exothermic methane- or Fischer-Tropsch synthesis or from another suitable hydrocarbon synthesis. Further, during adsorption of carbon dioxide from a moist air/gas stream water is adsorbed on the adsorption material, which is also regenerated by the temperature-vacuum-exchange process and can thereafter be made use of in either the carbon dioxide separator unit or the electrolysis arrangement. In this way, two plants which actually operate separately from one another are combined to form an overall system, the inventive method using the waste heat of the synthesis plant energetically in order to carry out the necessary thermal desorption.

The heat is removed from steam generated in the synthesis process. The heat contained therein has a high density and can also be temporarily stored.

The electrolysis device is a steam electrolysis (SOEC) operating with regeneratively generated electric energy for producing hydrogen, from which the generated heat from the cooling of the oxygen and/or hydrogen gas stream is extracted and used to reverse the $CO_2$-adsorption process. The use of the heat from the water vapor electrolysis alone in the inventive sense is sufficient to cover up to 35% of the heat requirement of the carbon dioxide generator.

In the synthesis method excess accumulating and/or not usable residual gas is burned and the material and/or energy of the resulting flue gas is used, for which purpose the heat of the flue gas is used to reverse the adsorption process and/or the $CO_2$-containing flue gas is used as an air/gas stream or as an additive in the air/gas flow.

In particular, low-temperature waste heat with temperatures below 80° C. from different areas of the plant as well as from external sources can be used for the regeneration of the adsorbed water in the carbon recovery process, whereby a major part of the adsorbed water is regenerated and thus the heat consumption in the range of 90-130° C. can be significantly reduced.

A heat pumping process is used to increase the temperature of heat from the synthesis process and/or residual gas use and/or cooling in the electrolysis and/or further process waste heat. It is therefore proposed, to utilize heat or waste heat from different sources, wherein the temperature level is too low for the desorption of carbon dioxide, to increase the temperature level by a heat pump process and thereby make it useful for desorption. Thus, even low waste heat of the subprocesses is generally only for the first time made usable for the desorption process, whereby only a small amount of energy is required for the heat pump process.

The carbon dioxide generator is preferably operated continuously, wherein the carbon dioxide requirement of the synthesis process preferably, due to the fluctuations of available regeneratively generated electrical energy for hydrogen generation, is operated discontinuous and the recovered carbon dioxide is temporarily stored in a buffer storage. Under a continuous carbon dioxide recovery system operation, an overall system consisting of several smaller carbon dioxide power plants can be envisioned, whose overall output is correspondingly designed and whose individual necessary thermal desorptions are carried out chronologically successively, so that a quasi-continuous operation is formed.

The intermediate or temporary buffering of the carbon dioxide in a short-term storage and a long-term storage connected in parallel takes place with increased pressure.

The long-term intermediate buffering can be carried out by liquefying the carbon dioxide. The synthesis process is discontinuous due to fluctuations of available regeneratively generated electrical energy and the useful heat from the synthesis and the electrolysis for the carbon dioxide generator can be temporarily stored in a buffer storage.

In operating the carbon dioxide recovery system enriched water may be recovered within the carbon dioxide recovery system, wherein this water comes from the atmosphere and can be used for electrolysis for the production of hydrogen. As a rule, at least 1 mole of water is formed per 1 mole of provided carbon dioxide. As a result, a large part of the water requirement of the synthesis can already be covered by the carbon dioxide recovery system. This aspect thus represents a further independent optimization, which can additionally be seen.

In a preferred embodiment in addition to hydrogen also carbon monoxide is obtained from carbon dioxide with the aid of electrolysis operated with regeneratively generated electric energy.

Furthermore, in this regard the electrolysis arrangement may be a steam electrolysis.

As a further addition to the recovery of carbon monoxide from carbon dioxide by means of the regeneratively generated electric energy operated electrolysis device, in addition to hydrogen, the steam can be recovered directly from the carbon dioxide-water vapor mixture extracted from the container during operation of the regeneration of the $CO_2$ recovery system, without that the water vapor is condensed in the meantime. In particular, this is also advantageous in combination with a water vapor electrolysis.

With regard to a production system, the production system for the production of synthetically produced methane/gaseous and/or liquid hydrocarbons, in particular for carrying out the production method in particular of a regeneratively generated electric energy driven electrolysis apparatus for producing hydrogen, a carbon dioxide recovery system for the production of carbon dioxide from an air/gas stream, wherein the carbon dioxide recovery system operates with an adsorbent material which by means of thermal desorption again releases the bound carbon dioxide and a methane or Fischer-Tropsch synthesis or other suitable hydrocarbon synthesis for synthesizing hydrogen and carbon dioxide to methane/gaseous and/or liquid hydrocarbons in which heat supply means and/or heat accumulator are provided for supplying and/or intermediate storage of heat from the synthesis of and/or heat the electrolysis arrangement and/or heat of a combustion device for residual gases from the synthesis process for the carbon dioxide recovery system, wherein the heat is used to carry out thermal desorption.

A steam drum is provided at the methane or Fischer-Tropsch synthesis reactor or the reactor of another suitable hydrocarbon synthesis, for separation of the steam-containing boiling water leaving the synthesis reactor from into boiling water and saturated steam, wherein transport means are provided for the saturated steam to a heat exchanger of a heating medium circuit of the carbon dioxide recovery system.

The electrolysis device is a steam electrolysis (SOEC—Solid Oxide Electrolysis Cell), wherein transport means for transporting heat from a cooling of the stream of formed hydrogen/oxygen are provided to a heat exchanger of a heating circulation of the carbon dioxide recovery system.

A heat pump arrangement is provided for increasing the temperature of usable waste heat from the electrolysis arrangement, the synthesis reactor and/or combustion device for residual gases.

Storage means are provided for storage and delivery to the methane or Fischer-Tropsch synthesis or to another suitable hydrocarbon synthesis of the carbon dioxide continuously produced in the carbon dioxide generator. Since the occurrence of these surplus electrical energy from regeneratively generated (wind, sun, water, etc.) electric energy varies with the time of day and the weather, which means that the carbon dioxide consumption and the accumulation of heat are also not constant. The plant for extracting carbon dioxide from ambient air is however, operated with constant power, so that, for adapting the fluctuating carbon dioxide consumption and heat production gas buffers are necessary for the storage of carbon dioxide and heat storage in a particular configuration. The storage means have a short-term gas buffer storage arrangement and/or a long-term gas buffer storage arrangement.

Figure 2:
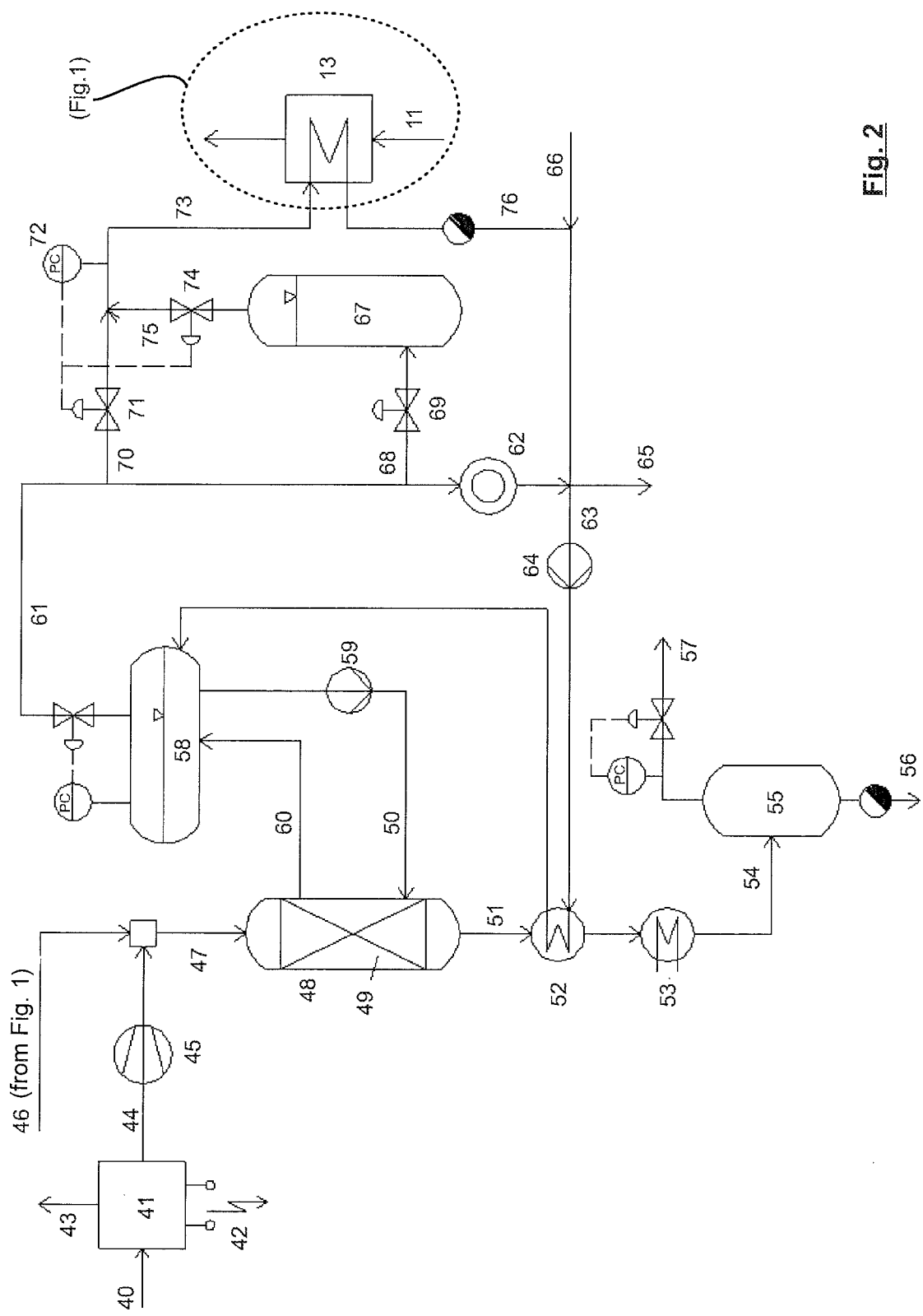
Figure 3:
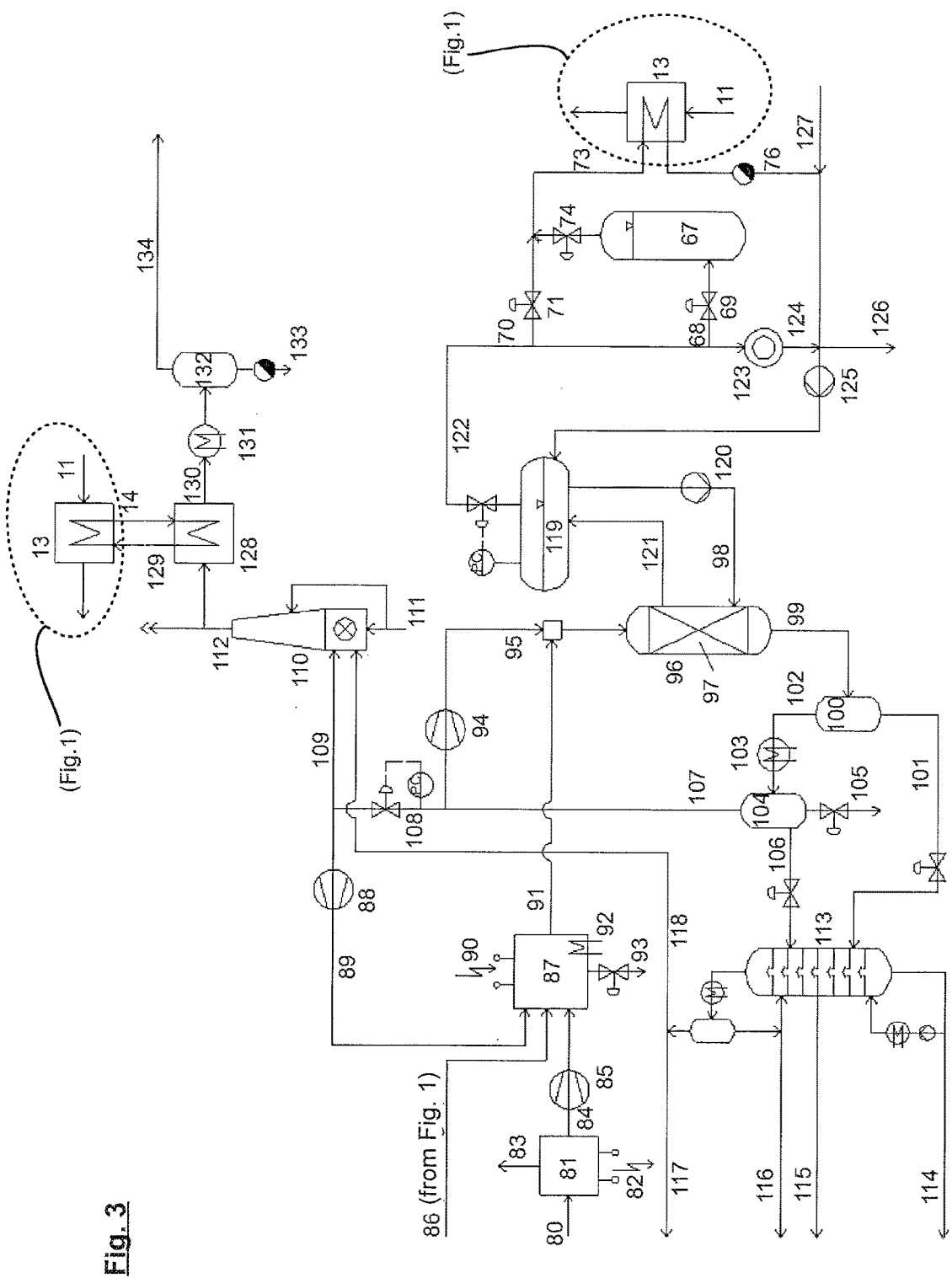
Figure 4:
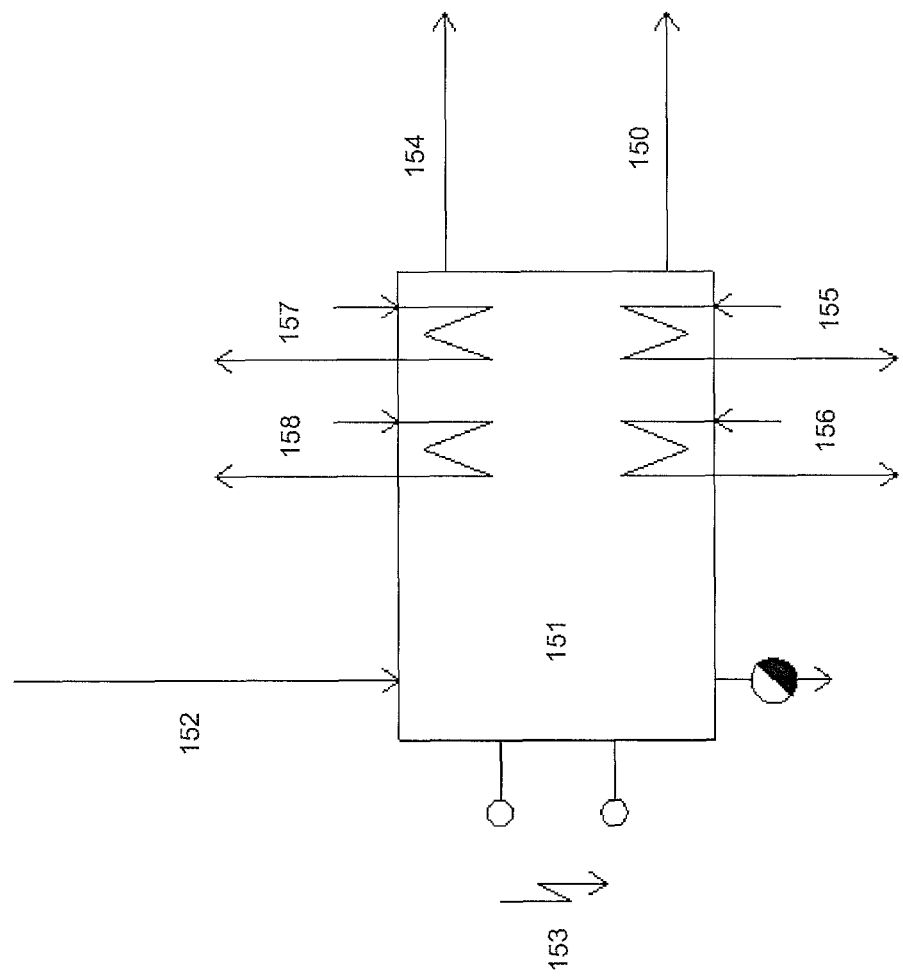
Figure 5:
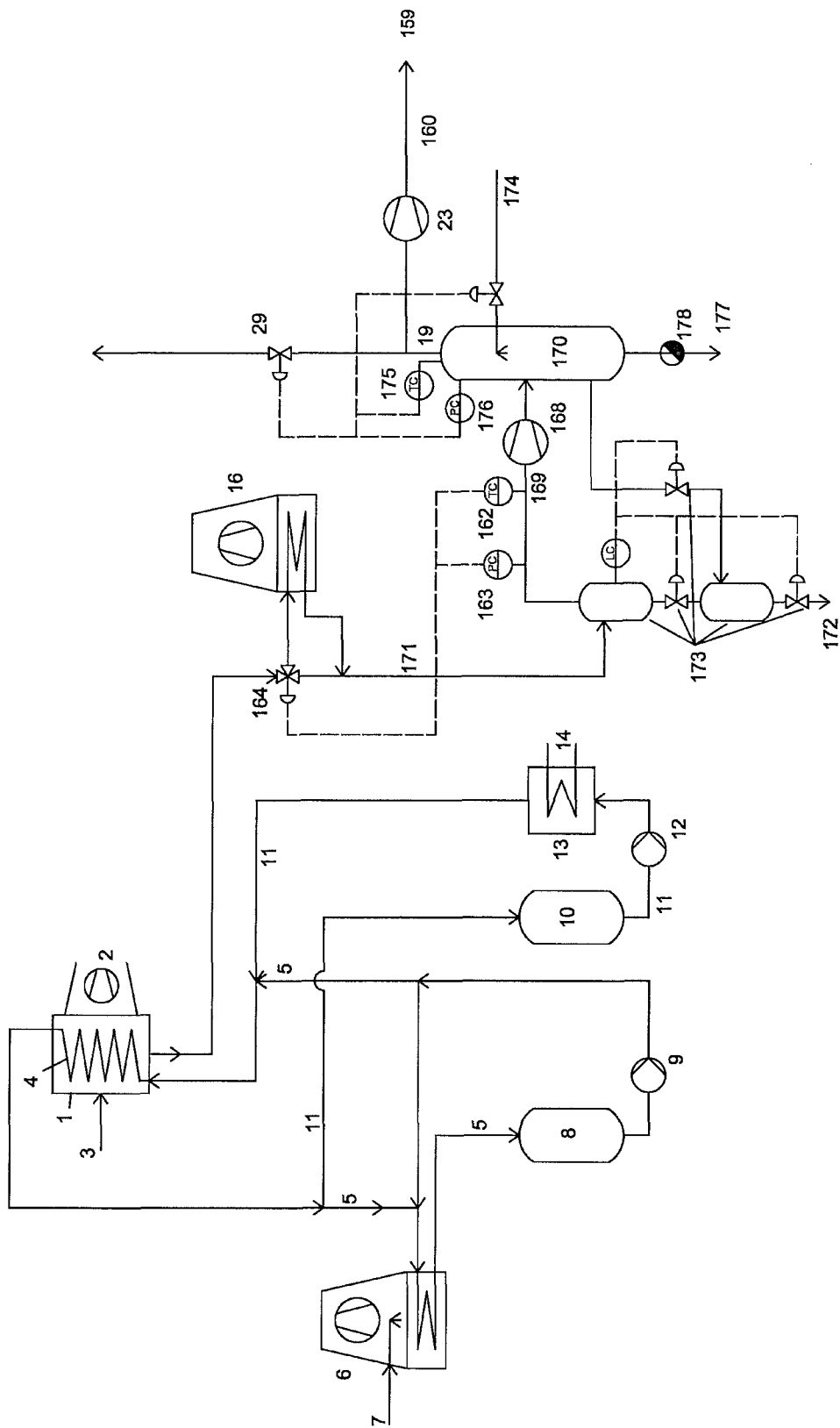
Figure 6:
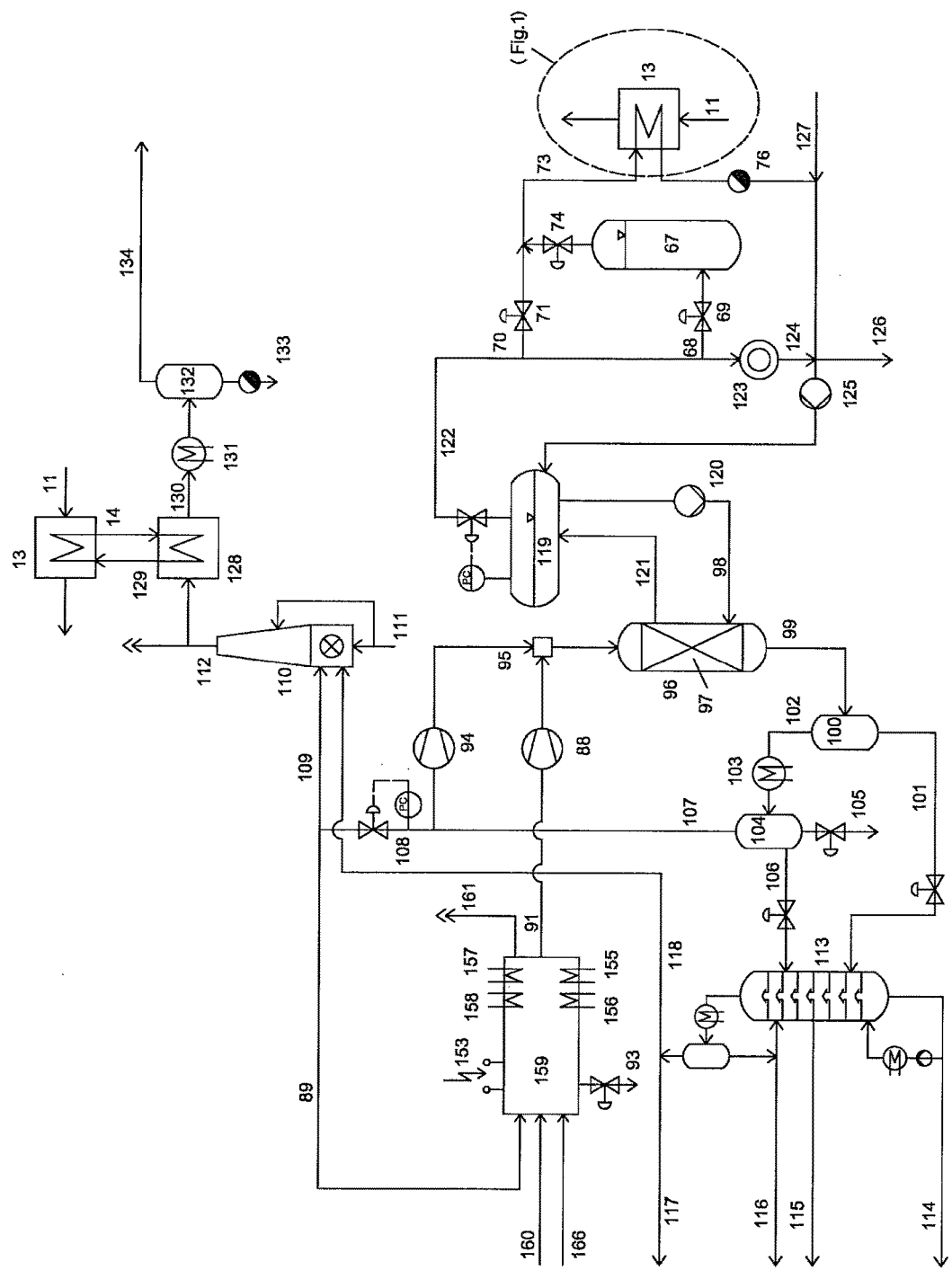
Figure 7:
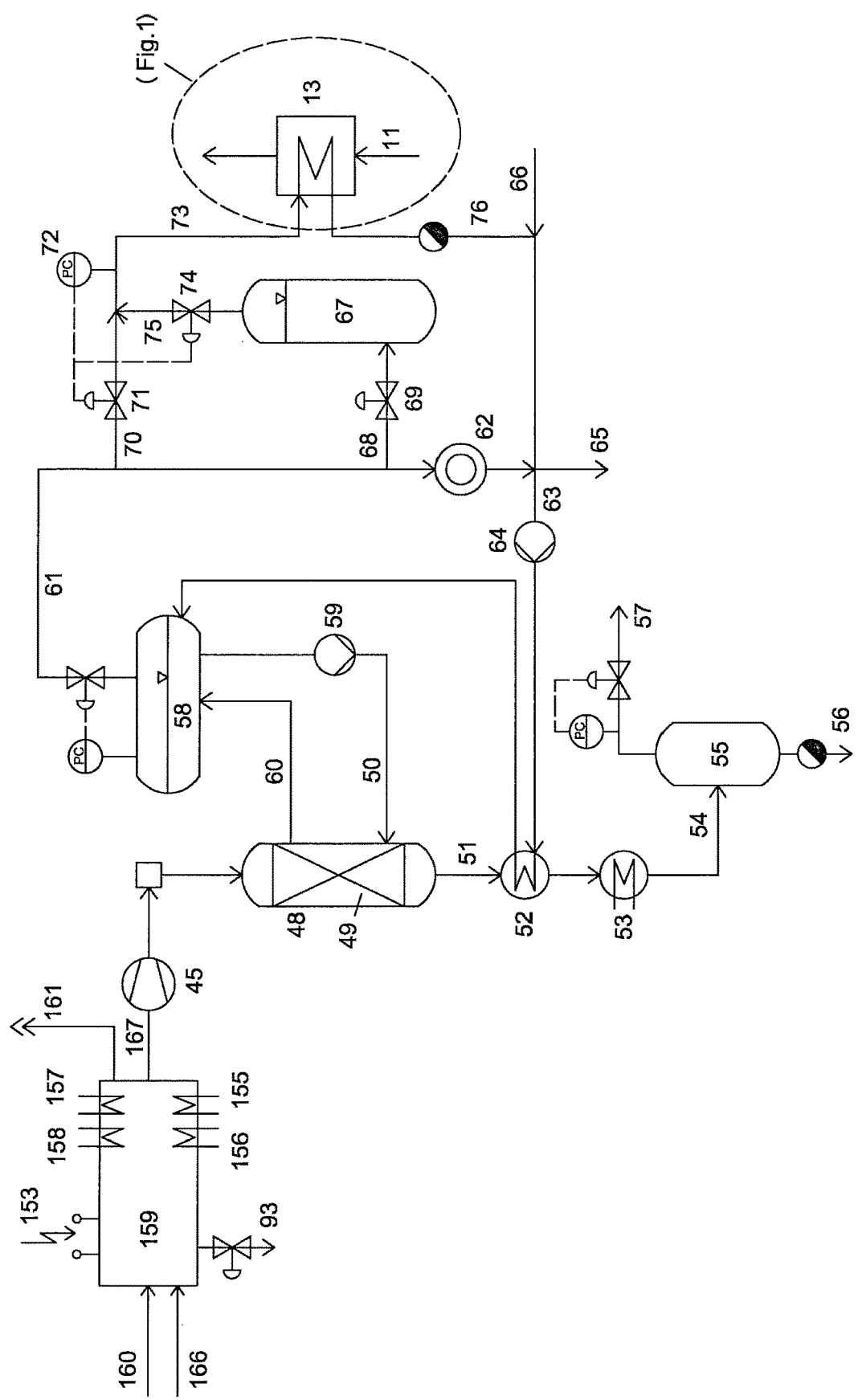
Figure 8:
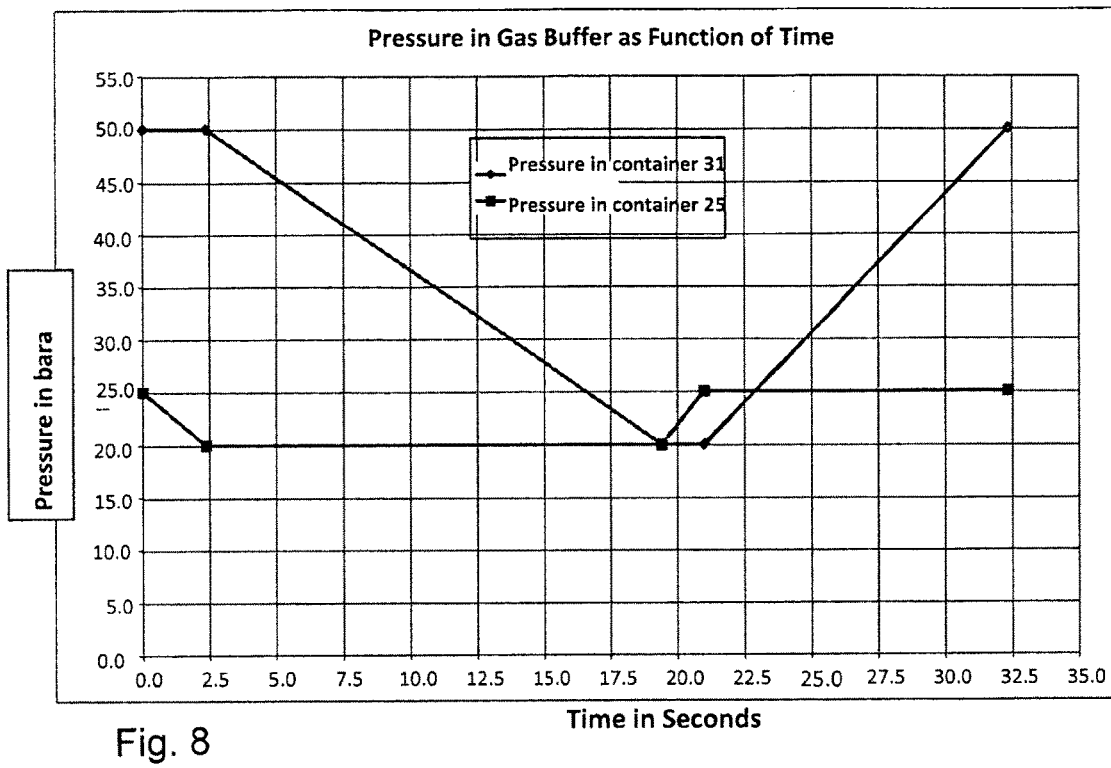
Figure 9:
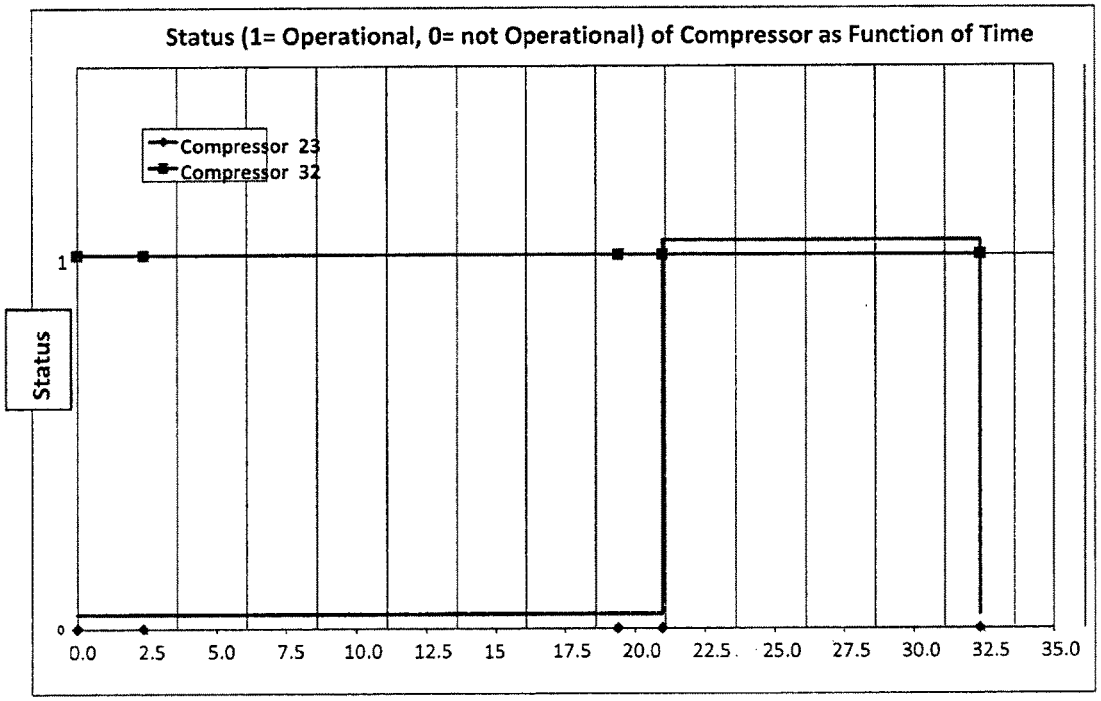
Figure 10:
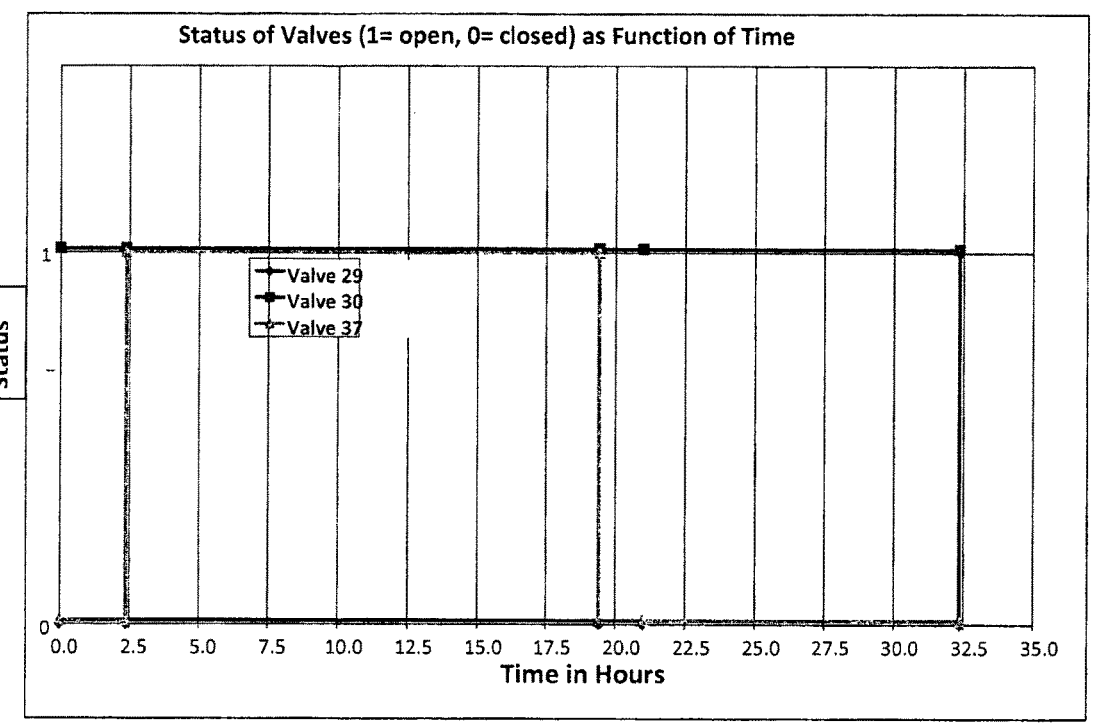
Figure 11:
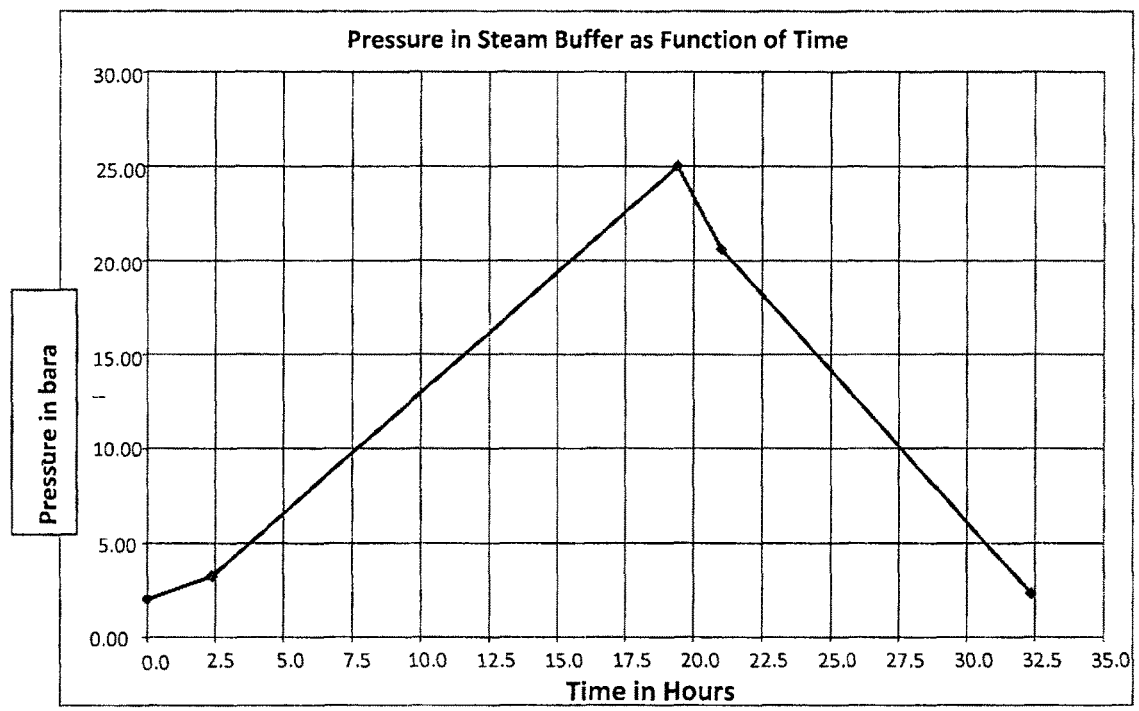
Figure 12:
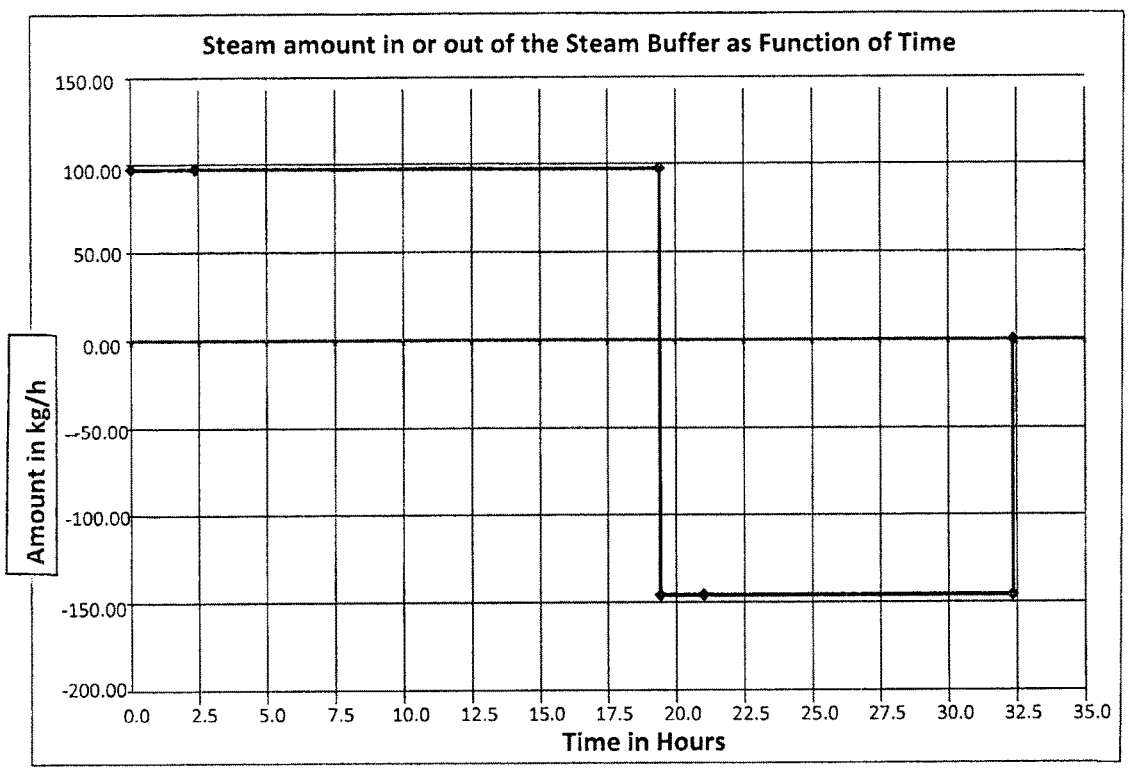
Figure 13:
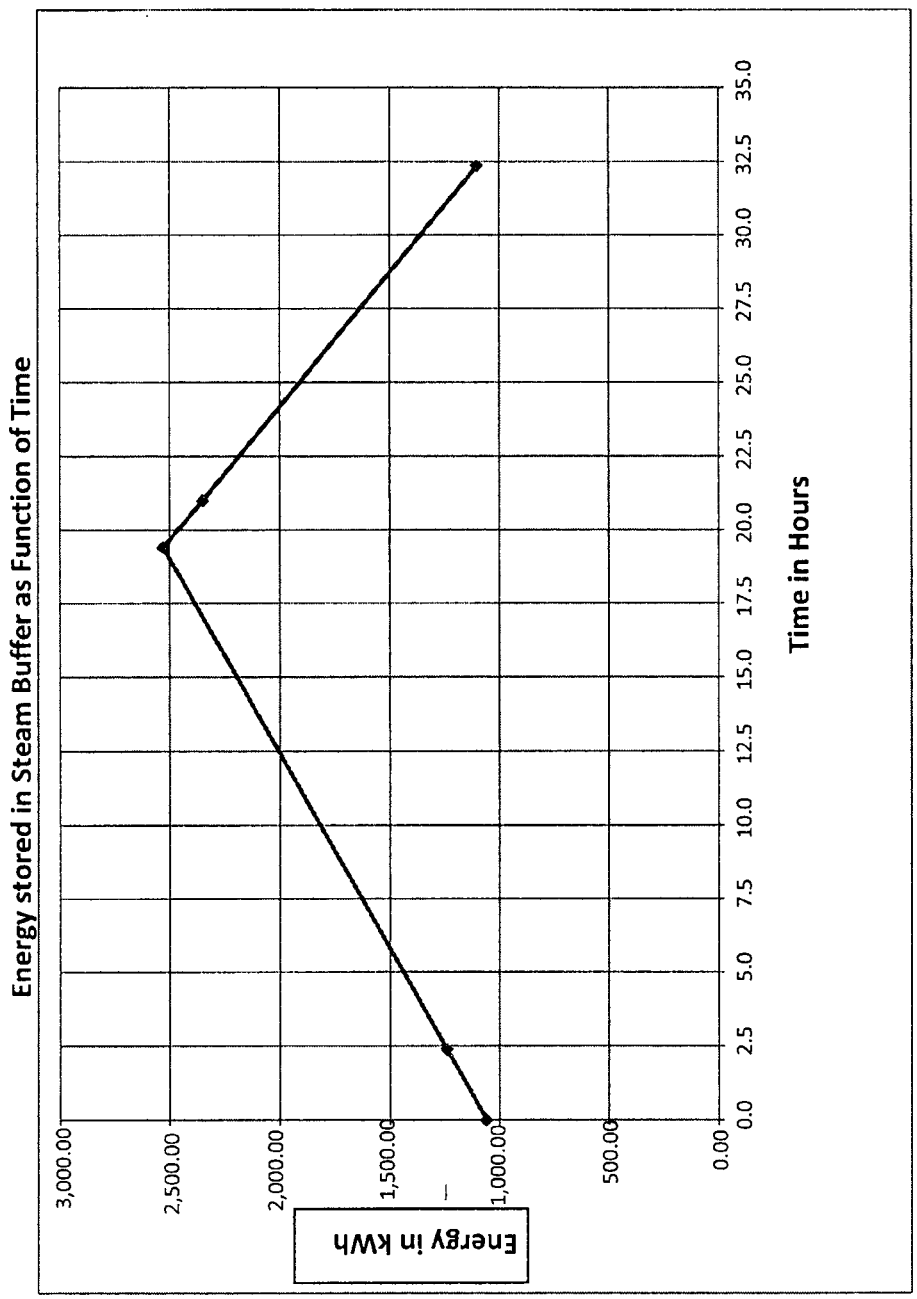

Embodiments of the invention will be described in detail with reference to the accompanying drawings in the description of the figures, which are intended to illustrate the invention and are not to be regarded as limiting:

In the drawings there is shown in:

FIG. 1 a schematic representation of one embodiment of a carbon dioxide recovery system part;

FIG. 2 a schematic representation of one embodiment of a methane production plant part;

FIG. 3 a schematic representation of one embodiment of a synthesis plant part by means of Fischer-Tropsch synthesis;

FIG. 4 a schematic representation of an embodiment of a steam electrolysis based on a SOEC (Solid Oxide Electrolysis Cell);

FIG. 5 a schematic representation of the regeneration operation of one embodiment;

FIG. 6 a schematic representation of an embodiment of a co-electrolysis for Fischer-Tropsch synthesis, FIG. 7 a schematic representation of another embodiment of a co-electrolysis for methane production, and FIGS. 8 to 13 diagrams showing system parameters, namely, position of the valves, status of the compressors, pressure in the containers, excess amount of steam, pressure in Ruth buffer and amount of energy stored in Ruth buffer in Another Embodiment.

It should be noted at this point that the overall system consists of the carbon dioxide recovery system part (FIG. 1) and the plant part for methanation (FIG. 2) or synthesizing (FIG. 3). The water vapor electrolysis unit (FIG. 4) can be used both in the methanation plant section (FIG. 2) and in the synthesizing plant part with Fischer-Tropsch synthesis (FIG. 3).

In FIG. 1 is a schematic representation of an embodiment of a carbon dioxide recovery system part (FIG. 1).

The carbon dioxide recovery system part (FIG. 1) is used for the recovery of carbon dioxide 19 from the ambient air or a gas stream and provides, if needed, also condensed water 20 from the ambient air or a gas stream for further material use. For this, a carbon dioxide recovery system part is selected, which initially binds carbon dioxide via an adsorption operation from the air flow and subsequently releases the carbon dioxide by a temperature-vacuum-variation processes for further use.

Adsorption Operation:

Ambient air 3 is sucked by blower 2 through a vessel 1 filled with adsorbent material. The ambient air usually contains 0.04 Vol.-% carbon dioxide and, depending on the climate, a certain amount of water vapor. The carbon dioxide is enriched to a high proportion on the surface of the adsorbent material, which is preferably functionalized with amine groups. Further, water accumulates on the surface of the adsorption material, wherein usually at least 2 moles of water per 1 mole of carbon dioxide, but at a minimum at least 1 mole per 1 mole of carbon dioxide, is adsorbed.

Regeneration operation by means of temperature-vacuum-variation method:

If the surface of the adsorber 1 is saturated or enriched with carbon dioxide, it must be regenerated.

First, vessel 1 is evacuated to a pressure of 20-400 $mbar_{abs}$, and subsequently heating fluid 11 is pumped out of heating medium container 10 at a temperature of 20-120° C. by means of heating pump 12 through a heat exchanger 13.

In the heat exchanger 13 the heating fluid 11 is heated by an external heat source 14 (the heat according to the invention comes from the parts according to FIG. 2 or FIG. 3 or FIG. 4) to 80-130° C. Subsequently, the heating fluid enters the vessel 1, where it transfers heat to the adsorption material via the heat exchanger surfaces 4. As a result of the transfer of heat, the bound carbon dioxide and water is desorbed and sucked out of the vessel 1 by means of liquid ring compressor 15.

The cooled heating fluid 11 runs back into the heating medium container 10, from which it can be fed again to the process.

The hot extracted mixture of carbon dioxide and water vapor is cooled in a cooler (e.g. cooling tower 16) and passes through the liquid ring compressor 15, into which cold condensate 17 is introduced in order to improve the suction effect and for further cooling, into the separation vessel 18.

In the separation vessel 18, the carbon dioxide 19 is separated from the condensate 17/20, which originates from the atmospheric humidity and was also deposited on the adsorber material, by gravity. A portion of the condensate, after cooling with coolant 21 in the cooler 22, is fed to the liquid ring compressor. The excess condensate 20 is discharged after the separation vessel 18.

The highly concentrated carbon dioxide 19 is supplied for further use to the plant parts shown in FIG. 2 or FIG. 3.

After the regeneration process the heat transfer surfaces 4 are flowed-through by a coolant.

The coolant 5 absorbs the sensible heat of the adsorption material and the vessel 1 and removes it from vessel 1. The heated coolant subsequently passes into a cooling tower 6, where the heat absorbed is released back into the environment. To improve the cooling effect, in particular at high ambient temperatures, water 7 in the cooling tower can be atomized onto the heat exchanger surfaces of the cooling tower, where it evaporates.

The cold coolant 5 is collected in a coolant tank 8 and from there is returned to the adsorber tank 1 by means of a coolant pump 9.

After the cooling of the vessel 1 and the adsorbing material below a temperature of maximum 50° C. tank 1 is ventilated and the adsorption process can be started anew.

Alternative regeneration operation by means of temperature-vacuum-variation processes for the decoupling of waste heat both in the temperature range 80-130° C. and in the temperature range 50-90° C.:

If the surface of the adsorber 1 is saturated or enriched with carbon dioxide, it must be regenerated.

First vessel 1 is evacuated to a pressure of 20-400 $mbar_{abs}$, then from the 10 Heating medium container heating fluid 11 by means of heating pump 12 through a heat exchanger pumped.

First, vessel 1 is evacuated to a pressure of 20-400 $mbar_{abs}$, and subsequently heating fluid 11 having a temperature of 20-50° C. is pumped out of heating medium container 10 by means of heating pump 12 through an additional heat exchanger which is arranged in series with the heat exchanger 13/14.

In the serially-connected additional heat exchanger, the heating fluid 11 is heated to 45-85° C. by an external heat source, wherein the heat originates according to the invention from the parts according to FIG. 2 or FIG. 3 or FIG. 4. Subsequently, the heating fluid enters the vessel 1, where it delivers heat to the adsorption material via the heat exchanger surfaces 4. As a result of the supply of heat a part of the adsorbed water and part of the adsorbed $CO_2$ is desorbed (and typically in the specified temperature range, the desorption of water takes place in preference to $CO_2$ desorption) and is extracted from the vessel 1 by a liquid ring compressor 15.

The cooled heating fluid 11 flows back into the heating medium container 10 from which it can be recycled back into the process.

Subsequently, heating fluid 11 is pumped at a temperature of 70-120° C. from the heating medium container 10 by means of heating pump 12 through the heat exchanger 13.

In the heat exchanger 13, the heating fluid 11 is heated to 80-130° C. by an external heat source 14 (the heat according to the invention coming from the parts according to FIG. 2 or FIG. 3 or FIG. 4). Subsequently, the heating fluid enters the vessel 1, where it delivers heat to the adsorption material via the heat exchanger surfaces 4. By the heat supply, especially carbon dioxide is desorbed and sucked out of the vessel 1 by means of liquid ring compressor 15.

The cooled heating fluid 11 flows back into the heating medium container 10 from which it can be recycled back into the process.

The hot extracted carbon dioxide is cooled in the cooling tower 16 and passes into the separation vessel 18 via the liquid ring compressor 15 into which cold condensate 17 is added to improve the suction effect and for further cooling.

In the separation vessel 18, the carbon dioxide 19 is separated by gravity from the condensate 17/20, which originated from the atmospheric humidity and was also deposited on the adsorber material. A portion of the condensate, after cooling with coolant 21 in the cooler 22, is fed to the liquid ring compressor. The excess condensate 20 is discharged after the separation vessel 18.

The highly concentrated carbon dioxide 19 is supplied for further use in the plant parts shown in FIG. 2 or FIG. 3.

After the regeneration process the heat transfer surfaces 4 are flowed through by a coolant. The coolant 5 absorbs the sensitive heat of the adsorption material and the vessel 1 and removes it from vessel 1. The heated coolant subsequently passes into a cooling tower 6, where the absorbed heat is released to the environment again. To improve the cooling effect, in particular at high ambient temperatures, water 7 in the cooling tower can be atomized onto the heat exchanger surfaces of the cooling tower, where it evaporates.

The cold coolant 5 is collected in a coolant tank 8 and from there is returned to the adsorber tank 1 by means of a coolant pump 9.

After the cooling of the vessel 1 and the adsorbing material below a temperature of maximum 50° C. vessel 1 is ventilated and the adsorption process can be started again.

Carbon dioxide preparation for subsequent use in a methane—or Fischer-Tropsch synthesis or other suitable hydrocarbon synthesis:

By the required regeneration of the adsorption material a continuous separation of carbon dioxide from the air can take place. However, a parallel connection of several adsorption vessels 1 and the associated cooling and heating circuits and a time-staggered operation enable very probably the transformation of the discontinuous process into a quasi-continuous process, so that this embodiment represents a particularly preferred embodiment.

The carbon dioxide 19 recovered quasi-continuously at ambient pressure from the $CO_2$ preparation process is compressed by a compressor 23, with a subsequent gas cooling 24 for discharging the compressor heat, to a pressure which is higher than the pressure in the subsequent synthesis plants, and then stored in a gas buffer 25.

The water condensate 26 accumulated as a result of cooling is removed via a condensate trap 27 from the gas buffer 25.

The control valve 29 serves to control the pressure in the vessel 18, which depends on the quantity of $CO_2$ discharged from the compressor 23.

If the compressor 23 takes less $CO_2$ from the vessel 18 than is produced in the $CO_2$-production, the control valve 29 opens and releases the excess $CO_2$ quantity to the atmosphere or to another intermediate storage, for example a gas bag.

If the compressor 23 takes more $CO_2$ than is produced, initially the control valve 29 closes, subsequently the transport capacity of the compressor 23 is reduced further, so that the pressure in the tank 18 remains constant at a predetermined value.

If the tank pressure 28 has reached its maximum permissible value, then the compressor 23 is turned off.

The removal of carbon dioxide from the container 25 occurs via the control valve 30, which maintains the pressure in the subsequent synthesis plant constant at a predetermined value.

If the pressure in the container 25 is below a permissible value, which must be higher than the pressure in the subsequent synthesis plant, the compressor 23 switches on again and fills the gas buffer 25.

The difference between the buffer pressure and extraction pressure, the buffer volume and the required $CO_2$ quantity per unit time are determined by the time that can be bridged with the buffer.

Since the additional pressure increase for gas buffering costs additional compression energy over the required operating pressure of the synthesis plant addition, this should not be too high for economic reasons.

That means that longer bridging or transitory period times are determined mainly by the buffer volume. Since this is limited, a buffer with a low excess pressure is only suitable as a short-term back-up to compensate for short-term pressure fluctuations.

In order to ensure a higher $CO_2$ hedge for longer periods of time, it is proposed to build, in parallel with the short-time buffer 25, a long term buffer 31, which operates at a higher pressure.

This long-term buffer 31, connected to the compressor 32 and the subsequent condenser 33 for condensation of the moisture in the gas which is removed as condensate 34 through the condensate trap 35 from the container 31, is filled with $CO_2$ from the container 25 to a pressure well above the operating pressure of the synthesis plant and the maximum pressure of the container 25.

The compressor 32 is only operated when the container 25 has already reached its maximum pressure. In this case, the capacity of the compressor 23 is not reduced, but operated together with the compressor 32 with rated power. Once the container 31 has reached the maximum pressure 36, the compressor 32 is turned off and the power of the compressor 23 is reduced according to the consumption in the synthesis plant.

In times of an increased $CO_2$-requirement in the synthesis plant, the carbon dioxide from the container 25 is first removed through the control valve 30. If the pressure in the container dropped below the operating pressure of the synthesis plant, that is, the container 25 is empty, the control valve 37 opens and the synthesis plant is supplied with $CO_2$ from the long term buffer 31.

In the case of reduction of the $CO_2$-requirement in the first synthesis plant the control valve 37 closes, the pressure 28 in the container 25 rises up to the maximum allowable value. Subsequently, the compressor 32 starts and fills the buffer 31 to the maximum pressure value 36, whereupon the compressor 32 shuts down. Upon further oversupply of $CO_2$, finally, the pumping capacity of the compressor 23 is reduced.

A further increase the buffer amount of $CO_2$ is possible when the $CO_2$ is liquefied and stored in liquid form. Due to the higher density, a higher amount of $CO_2$ is thus stored for the same volume.

The liquid storage is a special case of long-term buffer and is not specifically discussed in detail, however, this configuration is of great importance.

FIG. 2 shows a schematic representation of an embodiment of a methane production system part.

The production of methane from carbon dioxide and hydrogen, produced with electrolysis using regeneratively generated of electrical energy, is carried out according to the reaction by Sabatier:

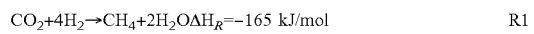

$$CO_2 + 4H_2 \rightarrow CH_4 + 2H_2O \quad \Delta H_R = -165 \text{ kJ/mol} \qquad R1$$

Deionized water 40 is separated into oxygen 43 and hydrogen 44 in an electrolysis apparatus 41 with regeneratively produced electrical energy 42. Oxygen 43 is transferred for use or if unused is discharged to the environment.

The hydrogen 44 is compressed in a compressor 45 to process pressure, and is mixed with carbon dioxide 46, which is already available at process pressure, and is supplied as a mixed gas 47 to a synthesis reactor 48.

The synthesis reactor 48 is filled with a sufficient quantity of a suitable catalyst 49 and, as the Sabatier reaction is exothermic, is cooled with boiling water loop 50.

The cooling temperature and thus also the boiling water pressure are chosen such that a high conversion of carbon dioxide to methane takes place.

This high turnover is usually achieved when the reaction gas 51 leaves the reactor 48 at a temperature of about 250 to 300° C.

After the reactor 48, the reaction gas is preferably cooled to low temperatures, in order to separate the water of reaction from the gas mixture. The cooling initially takes place in a heat exchanger 52 in which the cold feed water is preheated. The required low temperatures are ultimately achieved in a cooler 53 operated with coolant.

The cold gas mixture 54 passes into a separator 55, in which the reaction water 56 is separated from the methane-rich gas 57.

The generated methane 57 is supplied to the desired further use.

The boiling water 50 used for cooling is removed from the steam drum 58 and via pump 59 is supplied to reactor 48 for removing heat of reaction. The circulating amount of boiling water 50 was selected so that only a small part of the boiling water evaporates due to the heat absorption. The steamy boiling water leaving the reactor enters the steam drum 58, in which the separation between boiling water and saturated steam takes place. The saturated steam 61 is pressure controlled and removed from the steam drum 58 and supplied to a use, for example a heat sink 62. The steam condensate returned from the heat recovery is compressed by pump 64, preheated in the heat exchanger 52, and returned back into the steam drum 58. Possible loss of steam condensate 65 can be replaced by a new feed water 66.

According to the invention, the carbon dioxide 19 separated from the air 3 in the $CO_2$-producing plant part (FIG. 1) as carbon dioxide 46 for the production of methane 57 (FIG. 2), or as carbon dioxide 86 is employed for the production of liquid hydrocarbons (114, 115, 116, 117) (FIG. 3) with the aid of hydrogen 44 or 84, produced in a water electrolysis 41 or 81 by means of regeneratively generated electric energy (42, 82). Furthermore, steam 61 or 122 resulting in the synthesis process (FIG. 2 and FIG. 3) is used as a heat source 14 for the desorption of carbon dioxide deposited on the adsorbent material.

Heat storage for storing heat from the synthesis process (see FIG. 2 and FIG. 3):

The description is made on the basis of the example of methane synthesis according to FIG. 2. The steam storage in the synthesis of liquid hydrocarbons of FIG. 3 is analogous to the steam storage in the methane synthesis.

The steam pressure 61 evolved discontinuously in the synthesis plant is used as a heat source 14 for the desorption of the carbon dioxide accumulated in the adsorber.

Due to the discontinuous operation of the synthesis plant (FIG. 2/3) because of the different availability of the regeneratively generated electrical energy, occasionally temporarily an excess of steam occurs, which cannot be used in the desorption (FIG. 1). At other times, in which the synthesis plant (FIG. 2/3) is operated with lower load, insufficient steam is available to supply the heat for the desorption (FIG. 1).

To even out the heat supply for desorption, steam pressure 61 accruing discontinuously in the synthesis plant (FIG. 2/3) is therefore stored in a heat accumulator 67. The heat storage unit 67 is for example a boiling water filled variable pressure buffer (Ruth buffer). Other suitable heat storages include layer storage, molten salt storage and thermochemical storage.

During the charging process the excess pressure steam 68 generated in the synthesis is passed through the valve 69 into the buffer 67. The remaining steam 70 is reduced via the throttle valve 71 to the pressure 72 and is used as heating steam 73 for heating the heating medium 11 in the heat exchanger 13. At the beginning of the charging process boiling water and saturated steam are in the buffer 67 at the steam output pressure 72. Due to the supply of pressurized steam 68 the boiling water in the tank 67 is heated and the pressure in the container increases. The maximum possible pressure corresponds to the pressure of the supplied pressure steam 68. Due to the increase in pressure the steam portion is reduced and the water content increased in the container. The supplied heat is stored in the form of boiling water.

If there is a deficiency of heat for the $CO_2$ desorption, because the synthesis plant (FIG. 2/3) directly provides too little steam, the throttle valve 74 is opened and the desired difference in amount of steam 75 removed from the heat accumulator 67. Due to the withdrawal of steam, the pressure in the container 67 drops, and water in the boiling water tank is evaporated. A steam removal is possible up to the pressure 72. After discharging steam, the heat accumulator can be recharged.

The steam condensate 76 accumulating in the heat exchanger 13 is returned as feed water 63 back into the synthesis process.

Equipment for the generation of methane (FIG. 2) and liquid hydrocarbons (FIG. 3) from carbon dioxide and hydrogen, produced by regeneratively generated electric energy, are typically used as electric energy storage and are powered with regeneratively generated electric energy, which is superfluous to the power grid system, i.e., which would result, when not in use, for uneconomic isolation or even shutdown of conventional power generators.

In FIG. 3 a schematic representation of an embodiment of a synthesis plant part by means of Fischer-Tropsch synthesis is shown.

For the production of liquid hydrocarbons from carbon dioxide and hydrogen, produced in an electrolysis using regeneratively generated electric energy, a Fischer-Tropsch synthesis (FIG. 3) is used.

The conversion of carbon dioxide and hydrogen to hydrocarbons is carried out in two steps:

Step 1: reverse water-gas shift reaction for producing carbon monoxide containing synthesis gas

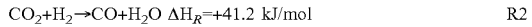

$$CO_2 + H_2 \rightarrow CO + H_2O \quad \Delta H_R = +41.2 \text{ kJ/mol} \qquad R2$$

Step 2: for example, Fischer-Tropsch synthesis for the creation of liquid hydrocarbons

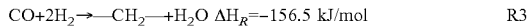

$$CO + 2H_2 \rightarrow -CH_2- + H_2O \quad \Delta H_R = -156.5 \text{ kJ/mol} \qquad R3$$

To increase the product yield a part can of light gaseous hydrocarbon from the Fischer-Tropsch synthesis can be worked up over a reform process back to synthesis gas and recycled back into the Fischer-Tropsch process:

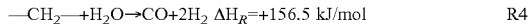

$$-CH_2- + H_2O \rightarrow CO + 2H_2 \quad \Delta H_R = +156.5 \text{ kJ/mol} \qquad R4$$

The reactions R2 and R4 are run in parallel in reactor.

Deionized water 80 is decomposed into oxygen 83 and hydrogen 84 in an electrolysis apparatus 81 using regeneratively generated electric energy 82. Oxygen 83 is supplied to a use, or is discharged unused to the environment.

The hydrogen 84 is compressed in a compressor 85 to process pressure, and together with carbon dioxide 86, which is already available at process pressure, as well as hydrocarbon-containing residual gases 89 recirculated by means of compressor 88 from the Fischer-Tropsch synthesis to a process 87 for performing the reverse water gas shift reaction (R2) and the reforming (R4).

The process heat required for both endothermic reactions is provided by means regeneratively generated electric energy 90.

The process 87 leaves the synthesis gas 91 with the required hydrogen-carbon monoxide molar ratio for the Fischer-Tropsch process. The excess reaction water separated by cooling 92 is discharged as a condensate 93 from the process.

The synthesis gas 91 is mixed with the recycle gas 95 back compressed in compressor 94 and fed to the Fischer-Tropsch reactor 96.

The Fischer-Tropsch reactor 96 is filled with a suitable catalyst 97 in sufficient quantity and, as the synthesis reaction R3 is exothermic, cooled with a boiling water circulation loop 98.

The cooling temperature and hence also the boiling water pressure are selected such that, depending on the selected catalyst, the conversion of carbon monoxide and hydrogen results in the desired product.

This desired product is generally achieved with the use of cobalt catalysts when the reaction product 99 leaves the reactor 96 with a temperature of about 220° C. The reaction product 99 is a mixture of reaction gas and long-chain, liquid hydrocarbons with a high number of carbon atoms. This mixture is separated in the high temperature separator 100 into liquid hydrocarbons 101 and hydrocarbon-containing gas 102.

The gas is further cooled in the cooler 103 and separated by gravity in separation vessel 104 into water of reaction 105, liquid hydrocarbons 106 and residual gas 107. The cooling and separation can take place in several cooling stages.

A portion 95 of the residual gas 107, used to increase the carbon monoxide conversion in the Fischer-Tropsch synthesis, is recompressed by compressor 94 and fed back again with the synthesis gas 91 to the reactor 96.

In order to avoid a too high accumulation of reaction gas constituents not participating in the Fischer-Tropsch ($CO_2$, $CH_4$, $C_2$ . . . , $N_2$), a partial stream of gas 108 must be removed from the Fischer-Tropsch process.

This part stream 108 can either be burned as the gas 109 in a combustion device 110 with air 111 making the flue gas 112, which is emitted to the environment, or partly recompressed with the compressor 88 and supplied as a stream 89 to the process 87 for the reprocessing of the hydrocarbons to synthesis gas. Also in this case is to avoid nitrogen accumulation in the overall process a partial stream is combusted in the combustion device 110.

The liquid hydrocarbons 101 and 106 separated in the Fischer-Tropsch process pass into a single or multi-stage product preparation 113, in which the hydrocarbons are processed into finished products having different properties. End products are for example wax 114, diesel 115, naphtha 116 and light hydrocarbon gases 117.

The residual gases 118 accumulating in the product preparation 113 are burned in the combustion device 110 with air 111 together with the residual gas 109 forming flue gas 112, which typically is discharged to the environment. However, this flue gas 112 from the combustion of residual gas is used in the plant for the production of liquid hydrocarbons (FIG. 3) as a heat source 14 for the desorption and as air substitute 3 with higher carbon dioxide content or for admixing with the air to increase their $CO_2$ content in the $CO_2$-production (FIG. 1).

The boiling water 98 used for cooling of the reactor 96 is removed from the steam drum 119 and supplied by pump 120 to the reactor 96 for removing the heat of reaction. The circulating amount of boiling water 98 was selected so that only a small part of the boiling water evaporates due to the heat absorption.

The steamy boiling water 121 leaving the reactor enters the steam drum 119, wherein the separation between boiling water and saturated steam occurs.

The pressure adjusted saturated steam 122 is discharged from the steam drum 119 and used, for example, supplied to a heat sink 123.

The steam condensate 124 returned from the heat recovery is increased in pressure by pump 125 and resupplied to the steam drum 119.

Possibly occurring steam condensate loss 126 can be replaced by a new feedwater 127.

Further, in FIG. 3 utilization of heat and $CO_2$ from the excess gas burner of a Fischer-Tropsch synthesis plant can be seen.

The flue gas 112 originating from the combustion of the residual gases 109 from the Fischer-Tropsch synthesis and light hydrocarbons 118 from the product treatment with air 111 is used as material and/or energy in the $CO_2$-producing (FIG. 1), since it was determined that this flue gas 112 can be used as the $CO_2$ source. Further, it was recognized that the thermal energy of the flue gases 112 can be used for the desorption process. For this purpose, the flue gas 112 is passed through a heat exchanger 128, which makes available heat 129 as heat for the $CO_2$ producing process via a heat transport circuit 14. The cooled flue gas 130 is further cooled in cooler 131 and supplied to the separation vessel 132, in that the condensed water of combustion is separated as waste water 133 from the gas stream 134. The gas stream 134 still contains carbon dioxide in addition to nitrogen and oxygen from the combustion air 111. Since the $CO_2$ concentration is substantially higher in the gas 134 than in the ambient air, this can be mixed into the air supply in the $CO_2$ production plant, and thus the $CO_2$ extraction from this mixture occurs in the $CO_2$ production plant more quickly and with less energy expenditure, respectively.

FIG. 4 shows a schematic representation of an embodiment of a steam electrolysis based on a SOEC (Solid Oxide Electrolysis Cell).

For the production of hydrogen 150 in a water vapor electrolysis 151 based on a SOEC (Solid Oxide Electrolysis Cell) water vapor 152 is recuperatively preheated by the hot product gases oxygen and hydrogen and at high temperatures, with the help of regeneratively generated electric energy 153, is decomposed into oxygen 154 and hydrogen 150.

The not recuperative usable heat is extracted from the hydrogen stream 157 and 158, as well as from the oxygen stream, with coolant 155 and 156.

If in the synthesis (FIG. 2 or FIG. 3) instead of a water electrolyzer (41, 81) a water vapor electrolyzer (FIG. 4) is used, then a fraction of the excess heat 155, 156, and 157 and 158 from the product gas cooling of the water vapor electrolysis 151 should be used as a heat source 14 for desorption of carbon dioxide.

Furthermore, heat storage for storing heat from the steam electrolysis is provided.

If a water vapor electrolysis 41 or 81 is used to produce hydrogen 44 and 84 instead of a water electrolyzer 151, generally the entire steam 61 or 122 generated in the synthesis is used in for the generation of hydrogen. Thus no or only a smaller proportion of the steam is available for heat supply for the $CO_2$ desorption.

In this case, part of the heat flow 158 or 156 extracted from the water vapor electrolysis for the final cooling of the oxygen 154 and the hydrogen 150 can be used as the heat supply 14 for $CO_2$ desorption.

Co-Electrolysis for Fischer-Tropsch Synthesis According to FIG. 3 and FIG. 6:

To produce a carbon monoxide and hydrogen-containing synthesis gas 91 from carbon dioxide 86, water 80 or water vapor 152 (corresponding to FIG. 4) and residual gas 89 then instead of the water electrolysis 81 or water vapor electrolysis 151 (corresponding to FIG. 4) and the RWGS/reforming process 87 a co-electrolysis (Co-SOC) 159 (corresponding to FIG. 6) are used, based on a Solid Oxide Electrolysis Cell (SOEC), in which regeneratively generated electric energy 153 is used to convert water vapor and carbon dioxide of a steam-carbon dioxide mixture 160 into hydrogen and carbon monoxide containing synthesis gas 91 and oxygen 161.

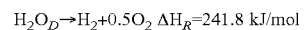

$H_2O_D \rightarrow H_2 + 0.5 O_2$ $\Delta H_R = 241.8$ kJ/mol

$CO_2 \rightarrow CO + 0.5 O_2$ $\Delta H_R = 283.0$ kJ/mol

By the high temperature in the co-electrolysis 159 of approximately 850° C. also the residual gas 89, which contains, in addition to hydrogen and carbon monoxide unreacted in the synthesis, also methane and other non-condensable hydrocarbons, especially by reforming the hydrocarbons with water vapor is worked up to synthesis gas.

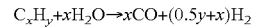

$C_xH_y + xH_2O \rightarrow xCO + (0.5y+x)H_2$

To provide the steam-carbon dioxide mixture 160 for co-electrolysis 159 there may be used, for example, carbon dioxide 86 from the $CO_2$ production unit described in FIG. 1 and water vapor 73 (corresponding to FIG. 3) according to the state of the art of the synthesis cooling (for example, from the document EP 2491998 A1). Therewith however no steam would remain available for the provision of heat in the heat exchanger 13 of the CO$_2$ production unit.

It is therefore proposed in accordance with FIG. 5, that in the regeneration operation, by means of a suitable vacuum pump 168, the from the vessel 1 drawn off hot carbon dioxide water vapor mixture with a water vapor content, depending on the relative air humidity of the respectively previous CO$_2$ adsorption, of 0.5 to 10, in particular 2 to 5 kmol per kmol carbon dioxide in the condenser 16 is only cooled to the extent, that so much water vapor remains in the hydrocarbon stream 19, as required for the subsequent co-electrolysis 159 (corresponding to FIG. 6) for producing a synthesis gas 91 with the mole ratio required a for the synthesis of H$_2$—CO.

The vacuum pump 168 has to compress the gas 169 present after cooler 16, saturated with water vapor, without condensation during the entire concentration process. Intercooling is permitted here only to the extent, that this does not lead to a condensing out of water. In a related embodiment even an overheating of the steam-containing gas by the compression process is desirable and advantageous, so that after the vacuum pump 168 in the buffer 170 and the piping up to the co-electrolysis 159 (FIG. 6) condensation is less liable to occur due to heat losses.

In a corresponding alternative embodiment, an at least partially intermediate cooling could well take place by means of a two-stage pumping arrangement.

Insulation and possibly accessory heating of the equipment to a temperature greater than the dew point of the steam-carbon dioxide mixture is advantageous in order to avoid condensation up to co-electrolysis.

Suitable vacuum pumps are, for example, dry-running (uncooled) reciprocating compressors and screw compressors.

Since the carbon dioxide-water vapor mixture 171 after the cooling in the cooler 16 is at the dew point, as a reference variable for controlling the water vapor content in the carbon dioxide, the temperature 162 depending on the pressure 163 in the gas mixture is used.

| At the dew point applies: | $p_D = p_s(t)$ $p_D + p_{CO2} = p_{tot}$ $r_D = p_D/p_{tot}$ | |
|---|---|---|
| with | $p_D$ | partial pressure of steam in the gas mixture |
| | $p_s(t)$ | boiling pressure of steam at the temperature |
| | $f_D$ | molar proportion or space proportion of steam in the gas mixture |
| | $p_{CO2}$ | partial pressure of CO$_2$ in the gas mixture |
| | $p_{tot}$ | total pressure |

There is regulated, for example, the amount of carbon dioxide-water vapor guided through a three-way valve 164 to the cooler 16 and/or the cooling performance of the cooler.

In this case, the water 172 condensed out in the condenser 16 must be removed from the gas stream 171 separated via a condensate lock system 173 ahead of the vacuum pump 168.

Possibly existing superheat in the gas 19 after the vacuum pump 168 can, by injection of externally preheated water 174, be used to further saturate the CO$_2$ with water vapor. As control variables for the amount of water, there may be used the temperature 175 and the pressure 176. Excess water 177 is removed from the vessel 170 via the trap 178.

If steam for the co-electrolysis is insufficient, because it cannot be covered completely through the water vapor content in the carbon dioxide 19 and possibly by externally preheated water 174, then addition steam 166 must be supplied from an external source to the co-electrolysis 159.

In an alternative embodiment of the carbon dioxide producing unit, the regenerating operation can be performed by flushing the vessel 1 with steam, either with or without simultaneously applied vacuum. In this case also there results a carbon dioxide-water vapor mixture, which can be suctioned from the vessel 1 and which can be cooled in the cooler 16 to the extent, that there is still included in the carbon dioxide stream 19 as much steam as required for the subsequent co-electrolysis 159 (corresponding to FIG. 6) for producing a synthesis gas 91 with a H$_2$—CO mole ratio as required for the synthesis.

Co-Electrolysis for Methane Production (FIG. 2 and FIG. 7):

In FIG. 7 there is shown a co-electrolysis 159 to produce a CO- and H$_2$-containing synthesis gas 167 and oxygen 161 from a H$_2$O—CO$_2$ mixture 160 from the CO$_2$ production using regeneratively generated electric energy 153.

In contrast to FIG. 2, where carbon dioxide 46 and hydrogen 44 from electrolysis 41 are used for production of methane according to the reaction 57

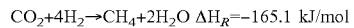
$CO_2 + 4H_2 \rightarrow CH_4 + 2H_2O$ $\Delta H_R = -165.1$ kJ/mol in FIG. 7 the conversion of carbon monoxide and hydrogen from the synthesis gas 167 takes place according to the reaction to methane:

$CO + 3H_2 \rightarrow CH_4 + H_2O$ $\Delta H_R = -206.2$ kJ/mol

The production of methane from carbon monoxide and hydrogen is prior art.

Overall, the present invention provides further advantages, namely:

By reducing the cooling of the desorbed carbon dioxide and thereby maintaining the water vapor from the air humidity in the carbon dioxide of the CO$_2$-production plant, a part of the heat used for desorption of carbon dioxide and water (evaporation) can remain mainly in the form of water vapor and be used for generation of hydrogen together with carbon monoxide from carbon dioxide in a co-electrolysis on SOEC basis.

It is in this case, through the cooling of accumulated waste water (condensate) and the use of additional water, the production of hydrogen in the electrolysis is avoided.

Furthermore, additional heat for evaporation of water in a water electrolysis, which requires application of electric energy, or for the external vaporization of water before a steam electrolysis is saved, whereby the efficiency of the overall process increases.

The use of a co-electrolysis instead of electrolysis and a RWGS process for producing synthesis gas reduces the necessary process steps for the production of synthesis gas to an electrolysis step, resulting in savings on equipment and so reduces investment costs.

By the in situ generation of the synthesis gas components CO and H$_2$ in the co-electrolysis at one temperature intermediate coolings are avoided and heat losses are reduced, resulting in the increase in efficiency of synthesis gas production and further increasing the efficiency of the overall process and thus reducing operating costs.

ANOTHER EMBODIMENT

In the following the description of the invention occurs with reference to a specific embodiment with reference to the diagrams shown in FIGS. 8 to 13 and the above-explained FIGS. 1 to 4:

A plant for production of carbon dioxide from the ambient air is to be coupled with a plant for the production of methane from carbon dioxide and hydrogen produced by water electrolysis and regeneratively generated electricity.

The $CO_2$ recovery plant has an annual capacity of 1,000 t $CO_2$/a, which corresponds, given an annual use of the facility of 8,000 hours, to a yield of 125 kg $CO_2$/h.

The $CO_2$-requirement of the methanation plant fluctuates depending upon access of regenerative produced excess electric energy in the electrical energy distribution network between 50 kg $CO_2$/h and 175 kg $CO_2$/h.

To balance the load fluctuations two $CO_2$-pressure buffers and one Ruth buffer are employed for storage of the steam from the synthesis.

The sizes of the buffer are:

| | | |
|---|---|---|
| $CO_2$-buffer (25): | 10 m³ | working pressure: 20 . . . 25 bara |
| $CO_2$-buffer (31): | 10 m³ | working pressure: 20 . . . 50 bara |
| Ruth buffer (67): | 12.7 m³ | working pressure: 2 . . . 25 bara |

The system parameters, namely, position of the valves 29, 30, 37, status of the compressors 23 and 32, pressure in the containers 25 and 31, excess amount of steam, pressure in Ruth buffer 67 and amount of energy stored in Ruth buffer 67 are shown in the diagrams shown in FIGS. 8 to 13 as a function of time.

In the nominal load case both systems (125 kg $CO_2$/h), the steam demand of the $CO_2$-production plant is 338 kg/h and the steam output of the methane generation system is 243 kg/h, that is, methane production system can cover only about 72% of the steam demand of the $CO_2$-production plant.

In the following it is assumed that a constant basic supply of steam for the $CO_2$-production plant of 95 kg/h is performed by a third party. Therewith, at the nominal load of both systems, the supplemental steam out of the methane production covers steam requirement for the $CO_2$ generation.

At time 0, both plants work in the rated load operation (125 kg $CO_2$/h). The state of the system is:

| | | |
|---|---|---|
| produced $CO_2$ quantity $CO_2$-generating plant: | | 125 kg/h |
| $CO_2$ consumption methane generation plant: | | 125 kg/h |
| position of the valves | 29: | closed |
| | 30: | open |
| | 37: | closed |
| state of compressors | 23: | in operation |
| | 32: | not in operation |
| pressure in the containers | 25: | 25 bara |
| | 31: | 50 bara |
| excess steam: | | 0 kg/h |
| pressure in Ruth storage tank | 67: | 2 bara |
| energy stored in Ruth buffer | 67: | 1,060.5 kWh |

The gas buffers 25 and 31 are both loaded. The produced $CO_2$ is quasi being pushed through container 25 with the compressor 23 and made available for methanation (FIG. 2).

The pressure in Ruth buffer has dropped to delivery pressure. The steam generated in the methanation is immediately made available for $CO_2$ production and therewith covers the current steam demand.

From time 0 to time 1 for 2.38 hours the yield of the methanation is raised to 175 kilograms $CO_2$/h.

The state of the system is:

| | | |
|---|---|---|
| produced $CO_2$ quantity $CO_2$-generating plant: | | 125 kg/h |
| $CO_2$ consumption methane generation plant: | | 175 kg/h |
| position of the valves | 29: | closed |
| | 30: | open |
| | 37: | closed |
| state of compressors | 23: | in operation |
| | 32: | not in operation |
| pressure in the containers | 25: | 20 bara |
| | 31: | 50 bara |
| excess steam: | | 97.2 kg/h |
| pressure in Ruth storage tank | 67: | 3.23 bara |
| energy stored in Ruth buffer | 67: | 1,240.5 kWh |

The pressure in the gas buffer 25 has dropped to 20 bara as a result of the height demand. The increased steam production of 97.2 kg/h results in a pressure increase in Ruth buffer to 3.23 bara.

From time 1 to time 2 for 17.03 hours (absolute 19.41 hours), the yield of the methanation is kept constant at 175 kg $CO_2$/h.

The state of the system is:

| | | |
|---|---|---|
| produced $CO_2$ quantity $CO_2$-generating plant: | | 125 kg/h |
| $CO_2$ consumption methane generation plant: | | 175 kg/h |
| position of the valves | 29: | closed |
| | 30: | open |
| | 37: | closed |
| state of compressors | 23: | in operation |
| | 32: | not in operation |
| pressure in the containers | 25: | 20 bara |
| | 31: | 20 bara |
| excess steam: | | 97.2 kg/h |
| pressure in Ruth storage tank | 67: | 25 bara |
| energy stored in Ruth buffer | 67: | 2,528.4 kWh |

The pressure in the gas buffer 31 is also decreased to 20 bara due to the greater consumption. The increased steam production of 97.2 kg/h results in a pressure increase in the Ruth buffer to 25 bara. The Ruth buffer has reached its upper pressure value.

From time 2 to time 3 for 1.59 hours (21.0 hours total), the performance of the methanation is lowered to 50 kg $CO_2$/h.

The state of the system is:

| | | |
|---|---|---|
| produced $CO_2$ quantity CO2-generating plant: | | 125 kg/h |
| $CO_2$ consumption methane generation plant: | | 50 kg/h |
| position of the valves | 29: | closed |
| | 30: | open |
| | 37: | closed |
| state of compressors | 23: | in operation |
| | 32: | not in operation |
| pressure in the containers | 25: | 25 bara |
| | 31: | 20 bara |
| excess steam: | | −145.8 kg/h |
| pressure in Ruth storage tank | 67: | 20.6 bara |
| energy stored in Ruth buffer | 67: | 2,348.6 kWh |

The pressure in the gas buffer 25 increased back to 25 bara due to the lower $CO_2$-consumption in the methanation. The pressure in the gas buffer 31 is still 20 bara. The reduced steam production in the methanation leads to a steam withdrawal from the Ruth buffer of 145.8 kg/h. This lowers the pressure to 20.6 bara.

From the time 3 to the time 4 for 11.35 hours (absolute 32.35 hours) the performance of the methanation remains constant at 50 kg $CO_2$/h.

The state of the system is:

| | | |
|---|---|---|
| produced CO₂ quantity CO2-generating plant: | | 125 kg/h |
| CO₂ consumption methane generation plant: | | 50 kg/h |
| position of the valves | 29: | closed |
| | 30: | open |
| | 37: | closed |
| state of compressors | 23: | in operation |
| | 32: | in operation |
| pressure in the containers | 25: | 25 bara |
| | 31: | 50 bara |
| excess steam: | | −145.8 kg/h |
| pressure in Ruth storage tank | 67: | 2.3 bara |
| energy stored in Ruth buffer | 67: | 1,101.3 kWh |

The compressor 32 buffers the container 31 with the excess $CO_2$ quantity back up to 50 bara.

The reduced steam production in the methanation leads to further steam withdrawal from the Ruth buffer of 145.8 kg/h. Thereby the pressure drops to 2.3 bara.

Thus, the initial state is reached again and the cycle can start again. The slightly higher pressure in the Ruth buffer is due to the fact that the steam having a higher specific enthalpy is returned than is withdrawn. By heat losses occurring in practice and/or additional coolers, this effect is compensated.

The time periods have been chosen here so that the buffer is in each case fully charged and then fully discharged. In practice, the time cycles corresponding to the excess electricity availability will look different, so the buffers reach only intermediate states.

When using a Fischer-Tropsch synthesis similarly as much steam is generated as in the methanation.

If the heat of the steam electrolysis, also additionally, is used, it can cover about 35% of the heat requirement for desorption.

LIST OF REFERENCE NUMBERS

FIG. 1 carbon dioxide generator
FIG. 2 methane synthesis plant
FIG. 3 Fischer-Tropsch synthesis plant
FIG. 4 water vapor electrolysis (SOEC)
1 container with adsorber material
2 speed
3 ambient air
4 heat exchanger surface
5 coolant
6 cooling Tower
7 water
8 coolant tank
9 coolant pump
10 heating medium container
11 heating fluid
12 heating pump
13 heat exchanger
14 heat source/heat
15 liquid ring compressor
16 cooling tower
17 condensate
18 separation vessel
19 carbon dioxide
20 condensate
21 coolant
22 cooler
23 compressor
24 gas cooling
25 gas buffer
26 water condensate
27 condensate trap
28 tank pressure
29 control valve
30 control valve
31 long-term buffer
32 compressor
33 cooler
34 condensate
35 condensate traps
36 pressure
37 control valve
40 deionized water
41 electrolyzer
42 electric energy
43 oxygen
44 hydrogen
45 compressor
46 carbon dioxide
47 mixed gas
48 synthesis reactor
49 catalyst
50 boiling water circulation
51 reaction gas
52 heat exchanger
53 cooler
54 gas mixture
55 separators
56 water of reaction
57 methane
58 steam drum
59 pump
60 boiling water
61 saturated steam
62 heat sink
63 feedwater
64 pump
65 steam condensate loss
66 feedwater
70 steam
71 throttle valve
72 pressure
73 heating steam
74 throttle valve
75 differential amount of steam
76 steam condensate
80 deionized water
81 electrolyzer
82 electric energy
83 oxygen
84 hydrogen
85 compressor
86 carbon dioxide
87 RWGS/Reforming process
88 compressor
89 residual gas
90 electric energy
91 synthesis gas
92 cooling
93 condensate
94 compressor
95 recycle gas
96 Fischer-Tropsch reactor
97 catalyst
98 boiling water circulation
99 reaction product
100 high temperature separator
101 liquid hydrocarbon
102 hydrocarbon-containing gas
103 cooler
104 separation vessel
105 water of reaction
106 liquid hydrocarbon
107 residual gas
108 partial stream of residual gas
109 gas
110 incinerator
111 air
112 flue gas
113 product preparation
114 wax
115 diesel -continued 116 naphtha
117 light hydrocarbon gas
118 residual gas
119 steam drum
120 pump
121 boiling water
122 saturated steam
123 heat sink
124 steam condensate
125 pump
126 steam condensate loss
127 feedwater
128 heat exchanger
129 heat
130 flue gas
131 cooler
132 separation vessel
133 sewage
134 gas flow
150 hydrogen
151 steam electrolysis
152 steam
153 electric energy
154 oxygen
155 excess heat
156 excess heat
157 excess heat
158 excess heat
159 co-electrolysis
160 $CO_2$-steam mixture
161 oxygen
162 temperature
163 pressure
164 faucet
165 faucet
166 additional steam
167 syngas
168 vacuum pump
169 water vapor saturated $CO_2$
170 containers
171 water vapor saturated $CO_2$ with condensate
172 condensate
173 lock system
174 preheated additional water
175 temperature
176 pressure
177 condensate, excess water
178 condensate traps

The invention claimed is:

1. A process for the synthesis at least one of gaseous and liquid hydrocarbons, the method comprising the steps:
producing an oxygen and hydrogen gas stream by electrolysis of water in an electrolysis device;
adsorbing carbon dioxide and water from atmosphere on an adsorption material in a carbon dioxide separator;
reversing the adsorption process and desorbing the adsorbed carbon dioxide and water in a temperature-vacuum-variation process wherein heat is introduced into the adsorption material and the pressure around the adsorbent material is lowered;
recovering the desorbed water and carbon dioxide;
supplying the recovered water to at least one of the carbon dioxide separator, a synthesis plant and the electrolysis device;
mixing hydrogen produced by electrolysis of water, recovered water and recovered carbon dioxide to obtain a crude synthesis gas; and
feeding the crude synthesis gas to the synthesis plant and carrying out an exothermic methane- or Fischer-Tropsch synthesis or other exothermic hydrocarbon synthesis in the synthesis plant to produce the at least one of gaseous and liquid hydrocarbons;
wherein the heat for the desorption of the adsorbed carbon dioxide and water from the adsorption material in the carbon dioxide separator is at least partly derived from the exothermic synthesis in the synthesis plant or from a cooling of the oxygen and hydrogen gas stream from the electrolysis device.

2. The process according to claim 1, wherein the heat is obtained from steam produced in the synthesis process.

3. The process according to claim 1, wherein the electrolysis device is a Solid Oxide Electrolysis Cell (SOEC) operating with regeneratively generated electric energy, and wherein heat obtained from cooling of the oxygen and hydrogen gas stream is used for reversing of the adsorption process.

4. The process according to claim 1, wherein excess and/or not usable residual gas accumulating in the manufacturing process is combusted to produce flue gas and at least one of material and heat energy from the flue gas is used, wherein at least one of
heat energy of the flue gas is used to reverse the adsorption process and
flue gas is used as the air/gas stream or as an additive in the air-/gas stream.

5. The process according to claim 1, wherein low-temperature waste heat at temperatures below 80° C. is used for regeneration of the adsorbed water in the carbon dioxide separator.

6. The process according to claim 1, wherein a heat pump process is used to transfer heat from the synthesis process, heat energy from combustion of residual gas and heat collected from cooling the oxygen and hydrogen stream produced in the electrolysis devide.

7. The process according to claim 1, wherein
the carbon dioxide recovery system is operated continuously,
the carbon dioxide requirement of the synthesis process is carried out discontinuously due to variations of available regeneratively generated of electrical power and
the carbon dioxide recovered (19, 46, 86) is intermediate stored in a buffer storage.

8. The process according to claim 1, wherein the synthesis process is carried out batchwise due to variations in available regeneratively generated electric energy and the usable heat for desorbing the adsorbed carbon dioxide is temporarily stored in a buffer storage.

9. The process according to claim 1, wherein water desorbed from the adsorption material in the carbon dioxide separator is used for electrolysis.

10. The process according to claim 1, wherein in addition to oxygen and hydrogen also carbon monoxide is recovered from carbon dioxide by means of the electrolysis device operated by regeneratively generated electric energy.

11. The process according to claim 10, wherein the electrolysis device is a steam electrolysis, and wherein the steam is obtained directly from a carbon dioxide-steam mixture taken from the vessel (1) during the desorption of the carbon dioxide without the water vapor being condensed in the meantime.

12. The process according to claim 7, wherein the intermediate buffering of the carbon dioxide occurs in a first buffer and a parallel thereto connected second buffer at a higher pressure, wherein the second buffering takes place via a liquefying of the evolved carbon dioxide.

13. The process according to claim 12, wherein the long-term intermediate buffering takes place via a liquefying of the desorbed carbon dioxide.

14. The process according to claim 1, wherein carbon dioxide from an air/gas stream exhausted from the synthesis plant is adsorbed on the amine-functionalized adsorption material in the carbon dioxide separator.

15. A process for the synthesis at least one of gaseous and liquid hydrocarbons, the method comprising the steps:
producing an oxygen and hydrogen gas stream by electrolysis of water in an electrolysis device;
adsorbing carbon dioxide (19, 46, 86) and water from atmosphere on an amine-functionalized adsorption material in a carbon dioxide separator;
reversing the adsorption process and desorbing the adsorbed carbon dioxide and water in a temperature-vacuum-variation process wherein heat is introduced into the adsorption material and the pressure around the adsorbent material is lowered;
recovering the desorbed water and carbon dioxide;
supplying the recovered water to at least one of the carbon dioxide separator, a synthesis plant and the electrolysis device;
mixing hydrogen produced by electrolysis of water, recovered water and recovered carbon dioxide to obtain a crude synthesis gas; and
feeding the crude synthesis gas to the synthesis plant and carrying out an exothermic methane- or Fischer-Tropsch synthesis or other exothermic hydrocarbon synthesis in the synthesis plant to produce the at least one of gaseous and liquid hydrocarbons;
wherein the heat for the desorption of the adsorbed carbon dioxide and water from the adsorption material in the carbon dioxide separator is at least partly derived from the exothermic synthesis in the synthesis plant or from a cooling of the oxygen and hydrogen gas stream from the electrolysis device.

* * * * *